(12) United States Patent
Totoki

(10) Patent No.: US 6,923,848 B2
(45) Date of Patent: Aug. 2, 2005

(54) COLLECTING APPARATUS OF FLOATING DUSTS IN ATMOSPHERE

(75) Inventor: Shinichiro Totoki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/882,621

(22) Filed: Jul. 2, 2004

(65) Prior Publication Data

US 2004/0231439 A1 Nov. 25, 2004

Related U.S. Application Data

(62) Division of application No. 10/322,677, filed on Dec. 19, 2002, now Pat. No. 6,807,874.

(30) Foreign Application Priority Data

| Jan. 21, 2002 | (JP) | 2002-011261 |
| Jan. 22, 2002 | (JP) | 2002-012322 |
| May 8, 2002 | (JP) | 2002-132613 |
| May 16, 2002 | (JP) | 2002-142012 |
| May 17, 2002 | (JP) | 2002-142817 |
| Jul. 3, 2002 | (JP) | 2002-194256 |
| Jul. 18, 2002 | (JP) | 2002-209713 |

(51) Int. Cl.$^7$ ............................. B03C 3/41; B03C 3/47
(52) U.S. Cl. .................. 96/26; 73/28.02; 73/864.71; 95/3; 95/59; 96/69; 96/96; 96/98; 96/413; 96/416; 96/418

(58) Field of Search ................... 96/26, 57, 63, 96/69, 75, 95–100, 413–418; 95/3, 59–61, 69, 79; 209/127.1, 131; 73/28.02, 864.71

(56) References Cited

U.S. PATENT DOCUMENTS

| 1,605,648 A | * | 11/1926 | Cooke | ............................. 95/79 |
| 1,849,198 A | * | 3/1932 | Miller | ............................. 95/67 |
| 1,997,125 A | * | 4/1935 | Soyez et al. | ................. 209/710 |

(Continued)

FOREIGN PATENT DOCUMENTS

| EP | 590841 | * | 4/1994 | |
| JP | 02-064435 | * | 3/1990 | ................. 73/865.5 |
| JP | 4-281863 | * | 10/1992 | ..................... 96/98 |
| JP | 05-172730 | * | 7/1993 | ................. 73/865.5 |

*Primary Examiner*—Richard L. Chiesa
(74) *Attorney, Agent, or Firm*—Manabu Kanesaka

(57) ABSTRACT

A collecting device for collecting particles floating in the atmosphere includes a collecting container; a pump for sucking the atmosphere into the collecting container; a discharge electrode disposed in the collecting container for generating single polarity ions to charge the particles in the collecting container; and a dust-collecting electrode for collecting the charged particles in the collecting container through a potential difference between the discharge electrode and the dust-collecting electrode. The dust on the dust-collecting electrode is measured and analyzed.

6 Claims, 14 Drawing Sheets

U.S. PATENT DOCUMENTS

Figure 1:
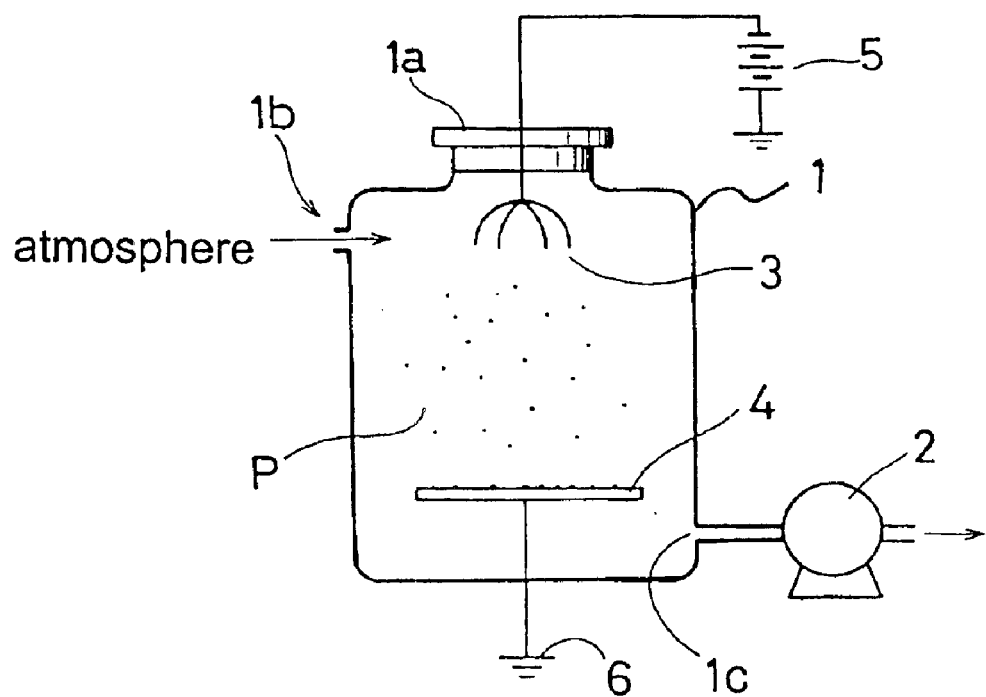

| | | | | |
|---|---|---|---|---|
| 3,473,118 A | * | 10/1969 | Tassicker et al. | 324/722 |
| 3,493,109 A | * | 2/1970 | Carta et al. | 209/11 |
| 3,853,750 A | * | 12/1974 | Volsy | 209/127.1 |
| 4,041,768 A | * | 8/1977 | Gibert et al. | 73/24.03 |
| 4,141,698 A | * | 2/1979 | Kihlstedt et al. | 95/69 |
| 4,597,781 A | * | 7/1986 | Spector | 96/52 |
| 4,725,294 A | * | 2/1988 | Berger | 73/863.22 |
| 4,772,297 A | * | 9/1988 | Anzai | 96/19 |
| 4,916,325 A | * | 4/1990 | Rood et al. | 250/573 |
| RE33,927 E | * | 5/1992 | Fuzimura | 96/62 |
| 5,217,510 A | * | 6/1993 | Logan et al. | 96/15 |
| 5,348,571 A | * | 9/1994 | Weber | 96/68 |
| 5,442,190 A | * | 8/1995 | Leck | 250/573 |
| 5,607,497 A | * | 3/1997 | Brown | 73/864.71 |
| 5,885,330 A | * | 3/1999 | Lee | 95/69 |
| 5,888,276 A | * | 3/1999 | Price et al. | 96/17 |
| 5,938,041 A | * | 8/1999 | Stencel et al. | 209/127.4 |
| 5,938,823 A | * | 8/1999 | Condit et al. | 96/16 |
| 5,944,875 A | * | 8/1999 | Stencel et al. | 95/57 |
| 5,980,614 A | * | 11/1999 | Loreth et al. | 96/63 |
| 6,004,375 A | * | 12/1999 | Gutsch et al. | 95/57 |
| 6,005,662 A | * | 12/1999 | Ence | 356/338 |
| 6,159,421 A | * | 12/2000 | Fujii | 422/4 |
| 6,187,271 B1 | * | 2/2001 | Lee et al. | 422/121 |
| 6,221,136 B1 | * | 4/2001 | Liu et al. | 96/66 |
| 6,230,551 B1 | * | 5/2001 | Burniston | 73/61.73 |
| 6,252,658 B1 | * | 6/2001 | Togawa et al. | 356/335 |
| 6,372,506 B1 | * | 4/2002 | Norton | 436/63 |
| 6,585,803 B1 | * | 7/2003 | Chang et al. | 95/70 |
| 6,589,314 B1 | * | 7/2003 | Page et al. | 95/32 |
| 6,674,528 B2 | * | 1/2004 | Adachi et al. | 356/336 |
| 6,807,874 B2 | * | 10/2004 | Totoki | 73/864.71 |
| 2003/0200787 A1 | * | 10/2003 | Totoki | 73/28.04 |

* cited by examiner

COLLECTING APPARATUS OF FLOATING DUSTS IN ATMOSPHERE

CROSS REFERENCE TO RELATED APPLICATION

This is a divisional application of a patent application Ser. No. 10/322,677 filed on Dec. 19, 2002, and now U.S. Pat. No. 6,807,874.

BACKGROUND OF THE INVENTION AND RELATED ART STATEMENT

The invention relates to a collecting device for collecting floating dusts in the atmosphere; a method for measuring a particle size distribution of the floating dusts collected by the collecting device; and a method for measuring a quantity, shape and component of the floating dusts in the atmosphere.

Among the fine particles floating in the atmosphere, those particles having a diameter less than 10 $\mu$m are called suspended particle matter (SPM). Although these floating dusts contain sands, they are mainly composed of black smokes, unburned materials, sulfur compounds and the like (35% of these is generated from diesel engine cars in the Kanto District, Japan), and it is said that they are highly toxic. The dusts from the exhaust gas from the diesel engine car are specially called diesel exhaust particles (DEP). Also, the particles floating in the atmosphere having a particle smaller than 2.5 $\mu$m are called micro-particulate matter (PM 2.5), and have been extensively researched and studied. It is said that the exhaust gas from the diesel engine car is a likely source of the PM 2.5.

In addition, as the particulate matters floating in the atmosphere, the yellow sands can be mentioned. The yellow sands are blown up by strong wind at inland desert of Chinese Continent and carried to Japan over the sea by the strong westerlies. Although particle diameters of the yellow sands differ depending on a location, the yellow sands in Chinese Continent near the desert have particle diameters in a range of 20 to 30 $\mu$m, and the particles reaching Japan far from the desert have diameters in the order of 4 to 5 $\mu$m.

Further, the particulate matters floating in the atmosphere include pollens. Recently, with increase in the number of people who suffered from a variety of pollinosis, information on the pollens floating in the atmosphere becomes important. The pollens of Japanese cedars and Japanese cypresses are said to be main causes of the pollinosis. The pollens of these plants have substantially a sphere shape with a diameter in the order of 30 to 50 $\mu$m.

As a method for measuring the floating dusts described above, there has been a method wherein the atmosphere is sucked in and passed through a filter to collect the floating dusts on the filter. Then, a microscope is used to observe the dusts for determining shapes and the number of the particles. There has been also a method wherein the floating dusts in a certain volume of the atmosphere are collected on the filter in the above-stated method, and weights of the filter before and after the collection are measured to obtain the quantity of the particles. In addition, there has been a method wherein the floating dusts collected on the filter in the same manner as described above are processed, and the extracted chemical components contained in the floating dusts are identified by a gas chromatograph mass spectrometer, liquid chromatograph mass spectrometer or spectrum analyzer.

Also, to measure a particle size distribution of the floating dusts (SPM) and micro-particulate matters (PM 2.5) in the atmosphere described above, a cascade-impactor type device has been practically used. The cascade-impactor type device utilizes an impacting process of suddenly changing a flow direction of a medium with the particles through colliding against a collecting plate, thereby separating the particles with a specific size from the medium. The cascade-impactor type device is structured such that a plurality of impactors, each having a 50% collecting efficiency at a specific particle diameter, is connected in series of multi-stage. A particle diameter of the dusts collected with the 50% efficiency at each stage represents an average particle diameter for each stage. Thus, the particle size distribution can be obtained from the quantity of the dusts collected from each stage.

Also, as a collecting method of the pollens floating in the atmosphere, a slide glass with an adhesive such as Vaseline coated on a surface has been used. The slide glass with the adhesive thereon is placed in the atmosphere, thereby allowing the pollens in the atmosphere to fall down thereon. The pollens adhered to the slide glass are observed by the microscope to thereby measure a shape, size, number, kind and the like.

Also, as a method for measuring a concentration of the floating dusts, there has been used a method wherein a certain volume of the atmosphere is sucked in and passed through a filter to trap the dusts therein. Then, weights of the filter before and after the collection are measured with an electronic balance or the like. The concentration of the floating dusts in the certain volume of the atmosphere can be determined from the weight difference.

Figure 14:

Also, as a device for effectively collecting the floating dusts in the atmosphere, an electrostatic-type particle collector has been known. In the electrostatic-type device, the particles floating in the atmosphere are charged by ions generated from a discharge electrode. A dust-collecting electrode with a different potential relative to the discharge electrode is disposed to collect the charged particles. As the discharge electrode, a discharge electrode as shown in FIG. 14 has been often used in the electrostatic-type particle collector. The discharge electrode is formed of a number, i.e. several hundreds, of metal wires, and the wires are bundled with a brush tip at one end.

In the collecting method using the filter to analyze SPM and PM 2.5 with the microscope or various chemical analyzing instruments, it is very difficult to extract the floating dusts individually. Therefore, in the case of the microscopic observation, the floating dusts adhered to the filter are observed with the microscope as they are. In this case, the particle image may be blurred because of a background filter image. Also, in the case of conducting various chemical analyses, since the floating dusts are difficult to remove from the filter, it is difficult to do the analyses. For example, in the case of a fluorescent X-ray analyzer, it is difficult to irradiate the X-ray only on the particles.

Further, it is difficult to conduct the spectrum analysis, since the floating dusts are not separated each other on the filter and electromagnetic wave is difficult to focus on a single particle. Also, the gas chromatograph mass spectrometer or the like is difficult to apply as the floating dusts are hardly separated from the filter.

In the conventional method for measuring the concentration of the floating dusts, the filter is easy to absorb water, thereby causing an error in measuring the floating dusts due to the absorbed water. Also, in this method, it is necessary to weigh the filter twice. Therefore, it is difficult to measure a real time change in the concentration, and the work is also troublesome.

Moreover, in the case that a laser diffraction particle size analyzer is used to determine the particle size distribution, it is necessary to irradiate a laser beam to the floating dusts having a concentration within a specific range to obtain appropriate diffracted or scattered light. In order to provide the floating dusts in the concentration range suitable for the measurement, for example, a specific quantity of the floating dusts may be collected through suction of the atmosphere for a certain period of time. However, the concentration of the floating dusts in the atmosphere is not constant and varies even during the collecting operation. Thus, at the time point when the collecting is completed, the quantity of the floating dusts is totally different from an expected value, and it is difficult to obtain a sample at a desired concentration.

Also, it takes long time to collect the pollens on the surface of the slide glass, for example, 24 hours, in the conventional method for collecting the pollens floating in the atmosphere. Also, a collected quantity per a specific period of time is influenced by wind and the like, so the collected quantity does not represent the actual pollen quantity existing in the atmosphere.

Also, when the microscope is used to observe the collected pollens, it is relatively easy to identify the shape and kind of the pollens. However, the information does not represent the whole pollens floating in the atmosphere since the. collected pollens are influenced by wind and the like. Further, it is necessary to measure the respective diameters of the pollens to obtain a particle size distribution of the pollens, resulting in a complicated work.

In the conventional measuring device based on the cascade impactor method for measuring the particle size distribution of the floating dusts, an upper limit of the measurement is theoretically in the order of 10 $\mu$m. In addition, the number of the collecting plates determines a resolution of the measurement. Therefore, even though it is desired that the particle size distribution be measured at a high resolution, there is a limitation.

In the conventional electrostatic-type particle collector as described above, it takes long time to manufacture the discharge electrode since a large number of metal wires need to be bundled together. In addition, it is necessary to have a step of making one end thereof in a brush shape, resulting in a high cost. Further, in addition to the cost, it is difficult to make the shape and structure of the discharge electrode uniform, resulting in a large variation in efficiency of generating the ions and collecting the particles in the particle collector.

In view of the above defects, the present invention has been made and an object of the present invention is to provide a device for collecting the floating dusts in the atmosphere, wherein the collected particles can be easily observed by the microscope and individual particles can be easily extracted for various analysis techniques. Another object of the invention is to provide a method for easily measuring the particle size distribution of the floating dusts in a wide range including particle diameter larger than 10 $\mu$m with a high resolution.

In addition, an object of the invention is to provide a method for clearly observing the floating dusts in the atmosphere by the microscope without influence of the background.

Also, another object of the invention is to provide a method for accurately measuring the quantity of the floating dusts in the atmosphere.

Further object of the invention is to provide a method for accurately identifying the chemical components contained in the floating dusts when analyzed by the gas chromatograph mass spectrometer and the spectrophotometer.

Further, an object of the invention is to provide a device for measuring a concentration of the dusts, wherein a real time change in concentration of the floating dusts in the atmosphere can be measured with a simple operation, and the collected floating dusts can be easily subjected to various measurements. Also, an object is to provide a collecting device for securely collecting the floating dusts in a specific concentration range.

Further, an object of the invention is to provide a collecting method wherein the yellow dusts in the atmosphere are effectively collected, and the collected dusts are easily subjected to the microscopic observation and various analyses. Another object of the invention is to provide a measuring method for measuring the particle size distribution and the concentration of the collected dusts at a high resolution.

In addition, an object of the invention is to provide a collecting device for securely collecting the pollens floating in the atmosphere without influence of the wind or the like. Another object of the invention is to provide a measuring device for easily and accurately measuring the particle size distribution of the pollens floating in the atmosphere as well as the shape, kind and number of the pollens floating in the atmosphere without influence of the wind or the like.

In the conventional electrostatic type particle collector, the discharge electrode is formed of a large number of metal wires, and one end of thereof is formed in a shape of the brush tip. An object of the invention is to provide an electrostatic type particle collector having a particle collecting efficiency equal to or better than that of the conventional device with a new type of electrode. The present invention can reduce a manufacturing cost and have good reproducibility, thereby improving the quality of the products.

The present invention is to provide a particle collector, wherein the dusts floating in the atmosphere can be collected effectively. The collected dusts can be easily preserved as they are. As a result, it is easy to observe the collected dusts with the microscope. In addition, the collected dusts can be individually extracted, thereby easily applying the various analyses including the laser diffraction-scattering type particle size distribution device.

Further objects and advantages of the invention will be apparent from the following description of the invention.

SUMMARY OF THE INVENTION

In order to attain the above objects, according to the present invention, a collecting device for collecting dusts floating in the atmosphere includes a collecting container; a pump for sucking the atmosphere into the collecting container; a discharge electrode disposed in the collecting container and generating single polarity ions to charge the dusts in the collecting container; and a dust-collecting electrode for collecting the charged dusts in the collecting container through a potential difference between the discharge electrode and the dust-collecting electrode. The dust-collecting electrode is structured such that a transparent coating made of a conductive material is applied to at least one surface thereof facing the discharge electrode.

According to the present invention, a method for measuring the dusts floating in the atmosphere is a method for determining a particle size distribution of the floating dusts collected by the above-described collecting device. After the dusts floating in the atmosphere are collected on the surface of the dust-collecting electrode, a laser beam is irradiated to the dust-collecting electrode. Accordingly, a spatial intensity distribution of the diffracted/scattered light from the dusts on the electrode is determined, thereby obtaining a particle size distribution of the dusts.

According to the present invention, the collecting device of the dusts floating in the atmosphere can attain the objects by charging the dusts floating in the atmosphere; and collecting the charged floating dusts on the dust-collecting electrode formed of a transparent plate, such as a glass plate and a plastic plate, with a conductive coating by using the potential difference between the discharge electrode and the dust-collecting electrode.

More specifically, in the collecting device of the dusts floating in the atmosphere according to the invention, the pump pulls the atmosphere into the collecting container. When the discharge electrode disposed in the collecting container generates the single polarity ions, the floating dusts contained in the atmosphere are charged. The charged dusts are attracted toward the dust-collecting electrode having the potential difference with respect to the discharge electrode in the collecting container. The dust-collecting electrode is structured such that a transparent conductive material is coated on at least the surface of the transparent plate, such as a glass plate and a transparent plastic plate, facing the discharge electrode. Thus, the dusts are accumulated on the flat surface of the transparent plate and can be subjected to the microscopic observation as they are, to thereby observe a clear particle image without any influence of the background image. Also, since it is possible to extract a single particle, the chemical analysis using various analyzing equipments, such as a fluorescent X-ray analyzer, can be easily carried out. Also, since the dust-collecting electrode is formed of the transparent plate with the transparent conductive coating, even if a large quantity of the charged dusts are accumulated, the constant potential is maintained by connecting the electrode to the ground. Thus, an effective collecting can be attained.

Also, according to the invention, the measuring method of the dusts takes advantage of the fact that the collected condition of the dusts by the above-mentioned collecting device satisfies the requirements for the laser diffraction-scattering method to conduct the particle size distribution measurement.

More specifically, it has been known that the laser diffraction-scattering method can measure a particle size distribution over a wide particle diameter range at a high resolution. In the particle size distribution measurement based on the laser diffraction-scattering method, the spatial intensity distribution of the diffracted/scattered light is obtained by irradiating the laser beam on the particles to calculate the particle size distribution of the particles. In the laser diffraction-scattering method, the particles to be measured need to be in a dispersed state and the diffracted/scattered light must have a sufficient intensity. The collecting device according to the present invention collects the floating dusts on the dust-collecting electrode in a dispersed state. Also, the dust-collecting electrode of the invention is formed of the transparent plate with the conductive coating to keep the potential constant, so that the floating dusts can be effectively collected. Thus, a quantity (concentration) of the floating dusts on the dust-collecting electrode can be controlled through setting a collecting time and the like.

Therefore, the dusts floating in the atmosphere can be collected on the dust-collecting electrode until a proper concentration is obtained. When the laser beam is irradiated directly to the dust-collecting electrode to which the floating dusts are adhered, the diffracted/scattered light has a sufficient intensity for calculating the particle size distribution. The particle size distribution of the floating dusts can be obtained at a high resolution over a wide particle range in the order of a sub-micron to 10 $\mu$m.

According to the present invention, a measuring method of the dusts floating in the atmosphere includes steps of charging the dusts floating in the atmosphere with the single polarity ions generated by the discharge electrode; collecting the charged particles on a solid dust-collecting electrode having a continuous surface through a potential difference between the discharge electrode and the dust-collecting electrode; and observing the collected floating dusts by a microscope to measure the shape and/or number of the particles.

Also, a measuring method of the dusts floating in the atmosphere according to the invention includes steps of charging the dusts floating in the atmosphere by the single polarity ions generated by the discharge electrode; collecting the charged particles on the solid dust-collecting electrode having a continuous surface through the potential difference between the discharge electrode and the dust collecting electrode; and measuring weights of the dust-collecting electrode before and after the floating dusts are collected thereon to thereby obtain a quantity of the dusts from the weight difference.

Further, a measuring method of the dusts floating in the atmosphere according to the present invention includes steps of charging the dusts floating in the atmosphere by the single polarity ions generated by the discharge electrode; collecting the charged particles on the solid dust-collecting electrode having a continuous surface through the potential difference between the discharge electrode and the dust collecting electrode; and identifying chemical components contained in the collected dusts by using one selected from or a combination of a liquid chromatograph mass spectrometer, a gas chromatograph mass spectrometer, a high-frequency induction binding plasma mass spectrometer, a spectrophotometer and a fluorescence X-ray analyzer.

Instead of collecting the floating dusts in the atmosphere by a filter, the present invention achieves the objects by charging the dusts with the single polarity ions from the discharge electrode, and collecting the charged dusts on the dust collecting electrode having the continuous flat surface, for example, a metal plate or a glass plate coated with a conductive material.

More specifically, when the floating dusts in the atmosphere are charged and electrically collected on the dust-collecting electrode having the continuous flat surface, the floating dusts are accumulated on the flat surface of the dust-collecting electrode in a dispersed state. Therefore, when the microscope is used to observe the collected dusts, a clear image of the respective particles can be easily obtained without an influence of the background image to thereby determine accurate shapes and the number of the particles.

Also, the dust-collecting electrode formed of the glass plate or metal plate does not absorb water. Therefore, the quantity of the collected floating dusts can be easily and accurately measured by measuring the weights before and after the dust-collecting electrode collects the charged dusts in the atmosphere.

Further, the floating dusts are collected on the dust-collecting electrode in a dispersed state, as described above, by collecting the charged dusts on the dust-collecting electrode having the continuous flat surface. Therefore, it is easy to apply the electromagnetic wave on the individual particle, and also the collected dusts can be easily extracted. Thus, the chemical components contained in the dusts can be easily and accurately identified with a liquid chromatograph mass spectrometer, a gas chromatograph mass spectrometer, a high-frequency induction binding plasma mass spectrometer, a spectrophotometer and a fluorescence X-ray analyzer.

According to the invention, a device for measuring a concentration of the dusts floating in the atmosphere includes a collecting container; a pump for sucking the atmosphere into the collecting container; a discharge electrode disposed in the collecting container and generating the single polarity ions to charge the floating dusts; a dust-collecting electrode formed of a transparent member for collecting the charged dusts in the collecting container through a potential difference with respect to the discharge electrode; a light irradiation device for irradiating light on the dust-collecting electrode; and a detector for detecting a transmitted light intensity of the light passing through the dust-collecting electrode, so that a result is output as a concentration of the floating dusts.

According to the invention, a collecting device of the floating dusts in the atmosphere includes a collecting container; a pump for sucking the atmosphere into the collecting container; a discharge electrode disposed in the collecting container and generating the single polarity ions to charge the floating dusts in the container; a dust-collecting electrode formed of a transparent member and having a potential difference with respect to the discharge electrode so that the charged dusts in the collecting container are collected thereon; a light irradiating device for irradiating light on the dust-collecting electrode; a detector for detecting a transmitted light intensity of the light passing through the dust-collecting electrode; and a control device for stopping the pump at a time when an output of the detector reaches a pre-set value.

Here, the dust-collecting electrode has a transparent electrode coated on a surface of a transparent plate, such as a glass plate and a resin plate. Alternatively, the dust-collecting electrode may have a structure where a transparent liquid, such as water, is contained in a dish or container formed of a glass plate on which a transparent electrode is coated, so that the floating dusts are collected in the liquid.

The present invention attains the objects by sucking the atmosphere into the collecting container, charging the floating dusts in the container with the discharge electrode, and collecting the floating dusts on the dust-collecting electrode formed of the transparent member, so that the concentration information of the floating dusts collected on the dust-collecting electrode can be obtained from the intensity of the transmitted light through the dust-collecting electrode.

More specifically, when the single polarity ions are generated from the discharge electrode while sucking the atmosphere into the collecting container, the floating dusts in the collecting container are charged. Then, the dusts are drawn and sequentially collected on the dust-collecting electrode, and accumulated uniformly on the surface thereof. Then, the light is irradiated on the dust-collecting electrode formed of the transparent member and the intensity of the transmitted light is detected. The detected value corresponds to the quantity of the dusts collected on the dust-collecting electrode. The total amount of the atmosphere sucked in the collecting container can be obtained from a flow rate of the pump and time. Thus, the concentration change of the dusts in the atmosphere with time can be obtained substantially at real time from the total amount of the sucked air and the detected value of the transmitted light intensity.

Also, the floating dusts are collected on the dust-collecting electrode, and then the transmitted light intensity through the dust-collecting electrode is detected, thereby obtaining the concentration information of the floating dusts in real time. Therefore, by automatically stopping the pump at a time when a value reaches a preset concentration, the floating dusts within a desired concentration can be collected.

According to the invention, a collecting device for collecting the floating dusts in the atmosphere includes a collecting container; a pump for sucking the atmosphere in the collecting container; a discharge electrode disposed in the collecting container for generating single polarity ions to charge the dusts in the collecting container; and a dust-collecting electrode having a different potential with respect to the discharge electrode so that the charged dusts in the collecting container are drawn and collected on the dust-collecting electrode. The dust-collecting electrode includes a transparent member provided with a recessed portion on a surface thereof, and a transparent electrode film coated on at least a bottom surface of the recessed portion.

The present invention attains the objects by charging the floating dusts in the atmosphere, and by collecting the charged dusts on the dust-collecting electrode through the potential difference. The dust-collecting electrode is provided with the recessed portion on the surface of a transparent member, such as a glass plate or a transparent plastic plate. Also, the transparent electrode is coated on the bottom surface of the recessed portion.

More specifically, in the collecting device of the present invention, when the pump sucks the atmosphere into the collecting container and the discharge electrode disposed in the collecting container generates the single polarity ions, the floating dusts in the atmosphere are charged. The charged dusts are drawn toward and collected on the dust-collecting electrode having a different potential with respect to the discharge electrode. The dust-collecting electrode has the recessed portion on the surface of the transparent member and the transparent electrode film is coated on at least the bottom surface of the recessed portion. Accordingly, the charged dusts are collected on the transparent electrode film in the recessed portion.

Since the floating dusts are collected in the recessed portion, a lid can cover the recessed portion so that the collected dusts can be easily preserved in a state as they are on the transparent member. Also, since the electrode is formed of the transparent member, the floating dusts can be subjected to the microscopic observation. Further, since the floating dusts can be easily extracted, the floating dusts can be subjected to various analyses. Also, the laser diffraction-scattering type apparatus can determine the particle size distribution of the floating dusts.

When the particle size distribution of the floating dusts is measured by using the laser diffraction-scattering type apparatus, before the spatial intensity distribution of the diffracted/scattered light from the collected dusts is measured, the standard particles dispersed in a medium liquid are sealed in the recessed portion of the dust-collecting electrode and the apparatus can be calibrated. Therefore, it is possible to eliminate variations in the particle size distribution measurements due to a shape of the dust-collecting electrode.

According to the present invention, in an electrostatic type particle collecting device, the discharge electrode generates the single polarity ions to charge the particles floating in the atmosphere, and the charged particles are collected on the dust-collecting electrode having a potential difference with respect to the discharge electrode. The discharge electrode is formed of a metal wire loop.

The present invention has been attained in view of a complicated conventional discharge electrode wherein several hundreds of metal wires are bundled and one end thereof is formed in a brush shape. The present invention provides an improved discharge electrode to meet the objects.

More specifically, the discharge electrode has a structure wherein a metal wire is formed in a loop shape. It was confirmed that the discharge electrode according to the invention has a discharging efficiency same or higher than that of the conventional discharge electrode. The discharge electrode has the simple loop shape structure, resulting in the high reproducibility. Thus, constant quality can be maintained, and the production cost can be reduced.

According to the present invention, in a collecting method of yellow sands, a pump sucks the atmosphere into a container; a discharge electrode disposed in the container generates the single pole ions to charge the floating dusts including the yellow sands in the container; and the charged particles are collected on a dust-collecting electrode having a potential difference with respect to the discharge electrode.

In the collecting method of the yellow sands according to the invention, the atmosphere is sucked into the container provided with the discharge electrode and the dust-collecting electrode therein. The yellow sand particles are charged by the single polarity ions from the discharge electrode to collect on the surface of the dust-collecting electrode. Therefore, it is possible to easily extract the yellow sand particles individually, so that the extracted yellow sand particles can be subjected to various analyses, and the observation by the microscope can be carried out easily.

Further, according to the present invention, a measuring method of the yellow sand particles includes steps of irradiating a laser beam on the particles obtained by the above-described collecting method in a dispersed state, measuring a spatial intensity distribution of diffracted/scattered light from the particles; and determining a particle size distribution and a particle concentration of a particle diameter range containing the yellow sand particles, from the measured results.

In the measuring method of the yellow sand particles according to the invention, it is possible to measure the particle size distribution and the particle concentration of the yellow sand particles at a high resolution by obtaining the particle size distribution of the yellow sand particles collected on the dust-collecting electrode, as described above, with the laser diffraction-scattering type apparatus.

More specifically, in the laser diffraction-scattering type apparatus, the laser beam is irradiated on the particles in a dispersed state to obtain the spatial intensity distribution of the diffracted/scattered light. The particle size distribution of the particles is obtained through the operations based on the scattering theory of Mie and the diffraction theory of Fraunhofer, from the spatial intensity distribution of the diffracted/scattered light. This is because the light intensity distribution complies with the scattering theory of Mie and the diffraction theory of Fraunhofer. According to the laser diffraction-scattering type apparatus, the particle size distribution can be obtained at a high resolution over a wide range of particle diameters by adjusting a concentration of a medium for dispersing the particles at a proper range.

However, when the laser beam is irradiated directly to the yellow sand particles in the atmosphere to measure the diffracted/scattered light, it is impossible to obtain the sufficient diffracted/scattered light for obtaining the particle size distribution due to a low concentration of the yellow sand particles in the atmosphere.

Therefore, in the present invention, the atmosphere is sucked into the container, and the particles including the yellow sand particles are charged in the container to collect on the dust-collecting electrode. Then the collected particles are dispersed with a concentration range suitable for the laser diffraction-scattering type measurement. The laser beam is irradiated to obtain the spatial intensity distribution. Thus, it is possible to measure the particle size distribution of the particles in the atmosphere over a wide range of the particle diameters like the normal laser diffraction-scattering type measurements. A pretest can be done to determine a particle diameter range of the yellow sand particles at a measurement location in advance. In other words, it can be confirmed that particles found in advance to be in the range are mainly the yellow sand particles. Thus, when only the particle size distribution in the particular range is measured, the result represents a correct particle size distribution of the yellow sand particles floating in the atmosphere.

Also, the laser diffraction particle size analyzer may be calibrated with particles whose concentration is known beforehand. As the quantity of the atmosphere sucked in the container can be easily calculated from a flow rate of the pump and an operation time, the concentration of the yellow sand particles in the atmosphere can be obtained.

According to the present invention, a collecting device for collecting pollens in the atmosphere includes a collecting container; a pump for sucking the atmosphere into the collecting container; a discharge electrode disposed in the collecting container for generating the single pole ions to charge the pollens in the collecting container; and a dust-collecting electrode having a potential difference with respect to the discharge electrode for collecting the charged pollens in the collecting container thereon.

Also, a measuring apparatus of the pollens in the atmosphere includes the above-described collecting device; a dispersing device for holding the pollens on the dust-collecting electrode in a dispersed state; an optical irradiation system for irradiating a laser beam on the pollens in the dispersed state; an optical measurement system for measuring a spatial intensity distribution of diffracted/scattered light from the pollens; and an operation device for calculating the particle size distribution of the pollens trapped on the dust-collecting electrode from the measured values.

Further, in a measuring method of the pollens in the atmosphere, a microscope is used to observe the pollens collected by the above-stated collecting device to determine the number, shapes and kinds of the pollens.

In the present invention, it is possible to collect substantially a whole quantity of the pollens in the atmosphere sucked in the container through the pump in a short time by electrically collecting the pollens without having any influence of wind or the like. Also, it is possible to quickly determine a particle size distribution of the pollens in the atmosphere by using the collecting device and the laser diffraction-scattering type apparatus. Further, it is possible to accurately measure the kinds, shapes and number of the pollens floating in the atmosphere by using the collecting device.

More specifically, when the pump sucks the atmosphere into the collecting container and the discharge electrode disposed in the collecting container generates the single polarity ions, the pollens in the atmosphere are charged. The charged pollens are drawn toward the dust-collecting electrode having a potential difference with respect to the discharge electrode in the collecting container, and collected on the dust-collecting electrode. By collecting the charged pollens in the collecting container on the dust-collecting electrode, substantially the whole quantity of the pollens in the atmosphere sucked in the trapping container can be collected. The result can represent a quantity of the pollens per unit volume of the atmosphere sucked in the collecting container without having any influence by the wind or the like.

Also, the measuring apparatus of the pollens according to the present invention is a combination of the above-described collecting device and the laser diffraction particle size analyzer. Since substantially the whole quantity of the pollens in the atmosphere sucked in the collecting container can be collected, a particle size distribution of the pollens floating in the atmosphere can be accurately measured.

More specifically, in the laser diffraction-scattering type apparatus, the laser beam is irradiated on the pollens in a dispersed state to obtain the spatial intensity distribution of the diffracted/scattered light. The particle size distribution of the pollens is obtained through the operations based on the scattering theory of Mie and the diffraction theory of Fraunhofer, from the spatial intensity distribution of the diffracted/scattered light. This is because the light intensity distribution complies with the scattering theory of Mie and the diffraction theory of Fraunhofer. According to the laser diffraction-scattering type apparatus, the particle size distribution can be obtained at a high resolution over a wide range of particle diameters, including 30 to 50 $\mu$m of the various pollens, by adjusting a concentration in a medium for dispersing the particles at a proper range.

However, when the laser beam is directly irradiated to the pollens naturally floating in the atmosphere, it is impossible to obtain the sufficient diffracted/scattered light for obtaining the particle size distribution due to a very low concentration.

According to the present invention, the collecting device electrically collects the pollens floating in the atmosphere. The collected pollens are dispersed in a concentration range suitable for the laser diffraction-scattering type measurement. The laser beam is irradiated on the pollens to measure the spatial intensity distribution. Thus, the particle size distribution of the respective pollens can be accurately measured at a high resolution over a wide range of particle diameters.

A dispersing device is formed of a combination of a dispersing tank for dispersing the collected pollens in a medium liquid, and an agitator or an ultrasonic vibrator. The laser beam is irradiated on the pollens dispersed in the medium liquid. The dust-collecting electrode in the collecting device is formed of a transparent member. A glass plate may be placed on the duct-collecting electrode for covering an upper surface thereof so that the pollens do not fall off. The laser beam may be irradiated directly to the pollens sandwiched between the dust-collecting electrode and the glass plate.

According to the present invention, a microscope is used to observe the pollens collected by the above-described collecting device to measure shapes, the number and kinds thereof. It is possible to collect samples representing all the pollens floating in the atmosphere and perform the observation without any influence of the wind and the like, so that the observation results represent information of all pollens in the atmosphere.

In this case, it is preferable that a transparent member is used as the dust-collecting electrode, so that the dust-collecting electrode with collected pollens thereon can be subjected to the microscopic observation as it is.

BRIEF DESCRIPTION OF THE DRAWINGS

FIG. 1 is a schematic view showing a structure of a collecting device for collecting dusts floating in the atmosphere according to an embodiment of the present invention;

FIG. 2 is a sectional view showing a structure of a dust-collecting electrode;

FIG. 3 is a schematic view showing a structure of a dust-collecting device for collecting dusts floating in the atmosphere according to an embodiment of the invention;

FIG. 4 is a block diagram showing a structure of a device for measuring dusts floating in the atmosphere according to an embodiment of the invention, wherein an optical structure and an electric structure are shown;

FIG. 5 is an explanatory view showing a microscope observation process for observing floating dusts collected on a dust-collecting electrode as shown in FIG. 1;

FIG. 6 is an explanatory view of a structure of an embodiment according to the invention;

FIG. 7 is a sectional view showing a dust-collecting electrode of an embodiment of the invention;

FIG. 8 is a schematic view showing a structure of an embodiment of the invention;

FIG. 9 is a sectional view showing a structure of a dust-collecting electrode of the embodiment shown in FIG. 8;

FIG. 10 is an explanatory view of a preserving method of floating dusts collected on a dust-collecting electrode of the embodiment shown in FIG. 8;

FIG. 11 is a diagram showing a structure of an apparatus in which a particle size distribution of the floating dusts collected on the dust-collecting electrode shown in FIG. 8 is measured by a laser diffraction particle size analyzer;

FIG. 12 is a schematic view showing a structure of an embodiment according to the invention;

FIG. 13 is a schematic view showing a structure of a device to evaluate a discharge efficiency of a discharge electrode according to the invention;

FIG. 14 is a view showing a shape of a conventional discharge electrode;

FIG. 15 is a schematic view showing a structure of an embodiment according to the invention, wherein a collecting device and a laser diffraction particle size analyzer for measuring a size distribution and a concentration of particles are combined;

FIG. 16 is a schematic view showing a structure of an essential part of the laser diffraction particle size analyzer; and FIG. 17 is a schematic view showing a structure of an essential part of a dry-type laser diffraction particle size analyzer.

DETAILED DESCRIPTION OF PREFERRED EMBODIMENT

Hereunder, embodiments according to the present invention will be explained with reference to the accompanying drawings.

FIG. 1 is a schematic view for showing a structure of an embodiment of a collecting device according to the present invention. A collecting container 1 has a lid 1a that opens and closes a top of the container. The collecting container also includes an inlet port 1b and a communicating port 1c. The communication port is connected to an inlet of a pump (compressor) 2, so that the pump 2 sucks the atmosphere into the collecting container 1 through the inlet port 1b in a state where the lid 1a is closed.

In the collecting container 1, a discharge electrode 3 is disposed at an upper portion thereof and a dust-collecting electrode 4 facing the discharge electrode 3 is positioned at a lower portion thereof. A high voltage is applied to the discharge electrode 3 from a high voltage source 5, so that the air near the discharge electrode 3 is ionized to produce single polarity ions.

The dust-collecting electrode 4 is a flat plate-shape electrode having a smooth surface, for example, a metal plate. The dust-collecting electrode 4 is connected to a ground potential 6.

Figure 3:
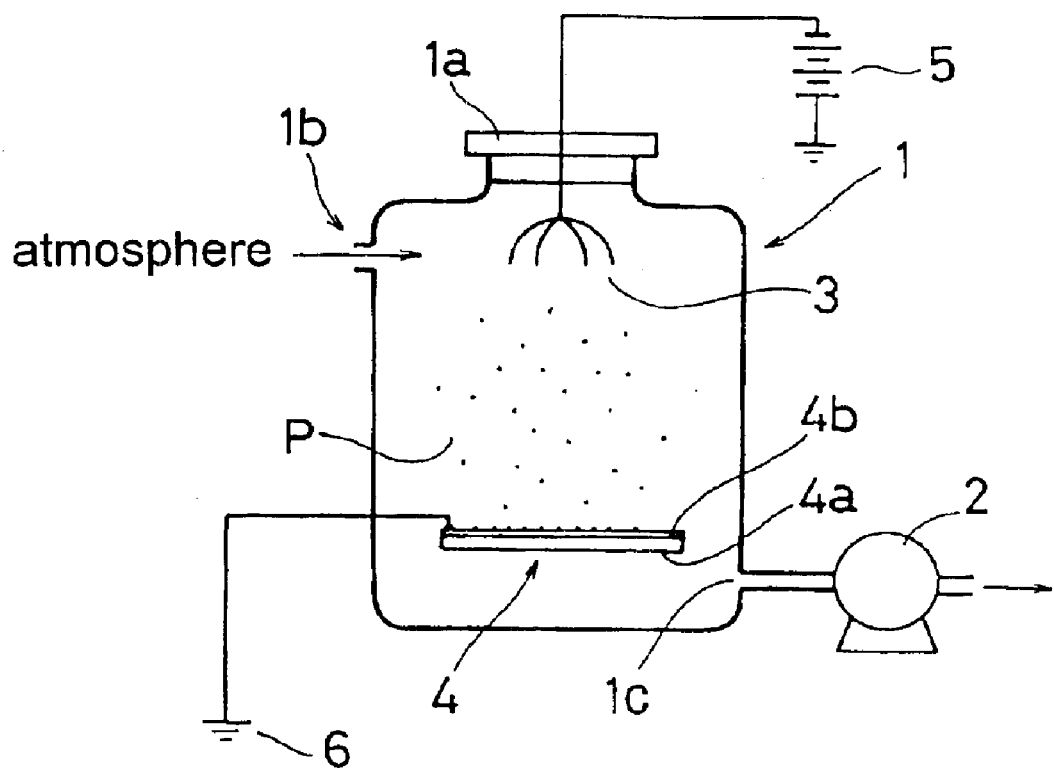
Figure 2:
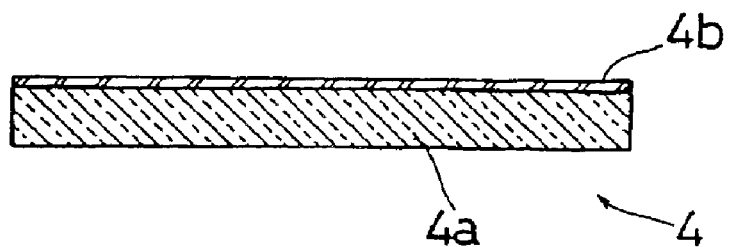

As shown in FIG. 2, the dust-collecting electrode 4 may be a transparent glass plate with a transparent coating 4b made of a conductive material. The conductive transparent coating 4b is connected to the ground potential 6, and disposed in the collecting container 1 to face the discharge electrode 3, as shown in FIG. 3. As a material of the conductive transparent coating 4b, for example, a known conductive material, such as ITO or $SnO_2$, can be used. Also, instead of the glass plate 4a, a transparent plastic, for example, an acrylic resin plate can be used.

In the above structure, when a high voltage is applied to the discharge electrode 3 while operating the pump 2, the surrounding air is ionized to produce the single polarity ions. The single polarity ions move to a side of the dust-collecting electrode 4 by a potential difference between the conductive transparent coating 4b and the discharge electrode 3. While moving, the single polarity ions contact and charge the floating dusts P in the atmosphere sucked into the collecting container 1. The charged floating dusts P are collected on an upper surface of the dust-collecting electrode 4 in a dispersed state at random due to the potential difference between the discharge electrode 3 and the conductive transparent coating 4b. The conductive transparent coating 4b on the upper surface of the dust-collecting electrode 4 is grounded. Therefore, even if a relatively large quantity of the-floating dusts P is collected, the potential difference does not change. Thus, the floating dusts P can be collected with a high efficiency.

As described above, the floating dusts P in the atmosphere are collected on the dust-collecting electrode 4 formed of the glass plate 4a and the conductive transparent coating 4b. Further, a laser diffraction particle size analyzer can easily measure a particle size distribution with a high resolution over a wide particle size range.

Figure 4:
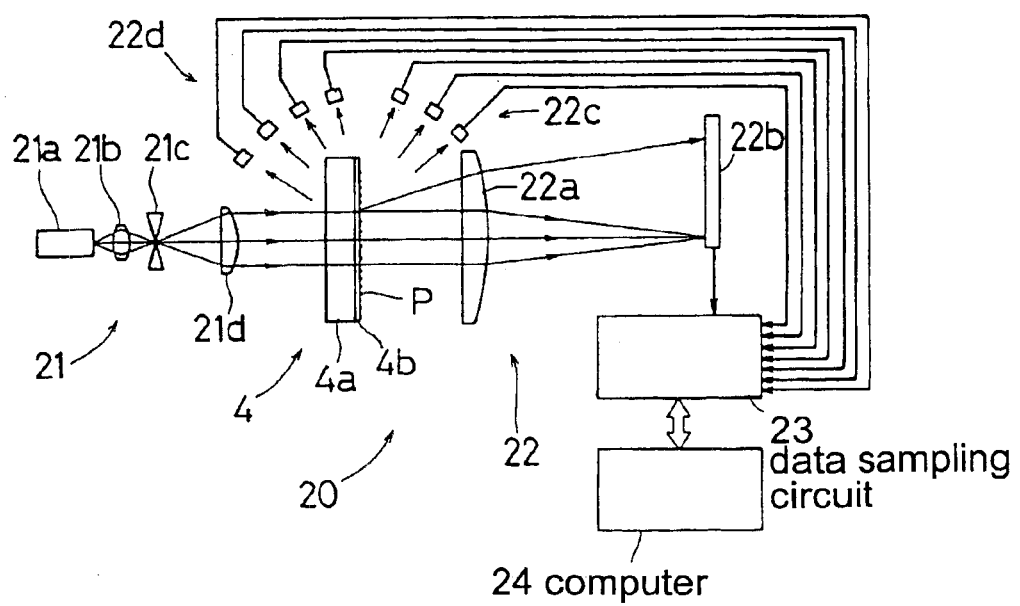

FIG. 4 is a schematic view showing a structure of a device for measuring the particle size distribution, wherein a schematic view showing an optical structure and a block diagram showing an electric structure are combined.

A laser diffraction-scattering type analyzer 20 includes an irradiation optical system 21 for irradiating parallel laser beams to the particles to be measured; a measuring optical system 22 for measuring a spatial intensity distribution of the diffracted/scattered light from the particles; a data sampling circuit 23 for sampling an output from the measuring optical system 22; and a computer 24 for calculating the particle size distribution of the particles from the spatial intensity distribution data of the diffracted/scatted light sampled by the data sampling circuit 23.

In the device as shown in FIG. 4, the dust-collecting electrode 4 with the floating dusts P collected thereon is disposed between the irradiation optical system 21 and the measuring optical system 22 so that the laser beams pass perpendicular to the dust-collecting electrode 4.

The irradiation optical system 21 includes a laser beam source 21a, a condenser lens 21b, a spatial filter 21c and a collimator lens 21d. The laser beams from the laser beam source 21a are irradiated as parallel rays to the floating dusts P on the dust-collecting electrode 4. The laser beams irradiated on the dust-collecting electrode 4 are diffracted and scattered by the floating dusts P adhering to the surface. The spatial intensity distribution of the diffracted/scattered light is measured by the measuring optical system 22.

The measuring optical system 22 includes a condenser lens 22a; a ring detector 22b; front wide-angle scattered light sensors 22c disposed outside the condenser lens 22a and the ring detector 22b; and side/backside scattered light sensors 22d disposed on a side and a backside of the dust-collecting electrode 4 (on a side of the irradiation optical system 21). The ring detector 22b is an optical sensor array formed of concentrically arranged light sensors with respectively different radiuses and light receiving surfaces in a shape of a ring-shape, ½ ring-shape or ¼ ring shape. It is possible to measure the spatial intensity distribution of the diffracted/scattered light within a predetermined front angle focused by the condenser lens 22a. Therefore, with the measuring optical system 22 composed of these sensors, it is possible to measure the spatial intensity distribution of the diffracted/scattered light from the floating dusts P adhered to on the dust-collecting electrode 4 over a wide range from a front micro-angle to a backward.

The light intensity signal for various angles measured by the measuring optical system 22 is amplified by the data sampling circuit 23 formed of amplifiers and A–D converters. The data is digitalized and input to the computer 24 as the spatial intensity distribution data of the diffracted/scattered light.

The computer 24 calculates the particle size distribution of the floating dusts from the spatial intensity distribution of the diffracted/scattered light through operations based on the scattering theory of Mie and the diffraction theory of Fraunhofer, which are known in the laser diffraction-scattering type measurement.

With the laser diffraction particle size analyzer 20, it is possible to measure the particle size distribution in a wide range of particle sizes, in the order of sub-micron to over 10 $\mu$m, at a high resolution. A small quantity of the floating dusts P on the dust-collecting electrode 4 is enough to obtain a sufficient intensity of the diffracted/scattered light. Thus, the particle size distribution of the floating dusts P in the atmosphere can be immediately measured at a high accuracy.

Also, the floating dusts P collected by the collecting device as shown in FIG. 4 are adhered on the dust-collecting electrode 4, which is the transparent flat plate, in a dispersed state. Thus, the floating dusts P can be subjected to a microscopic observation as they are without influence of any background image, thereby obtaining a clear image. Also, the floating dusts P collected on the dust-collecting electrode 4 in a dispersed state can be easily extracted as an independent particle. Also, since each particle is collected in an exposed state on the flat surface of the dust-collecting electrode 4, an electromagnetic wave, such as an X-ray and light, can be directly irradiated thereon, thus a chemical analysis using various analytical instruments can be easily applied.

In the collecting device shown in FIG. 4, if it is expected that the floating dusts P on the dust-collecting electrode 4 might fall off, another glass plate may be attached to the dust-collecting electrode 4 to hold the dusts, then the laser beam is irradiated.

Figure 5:
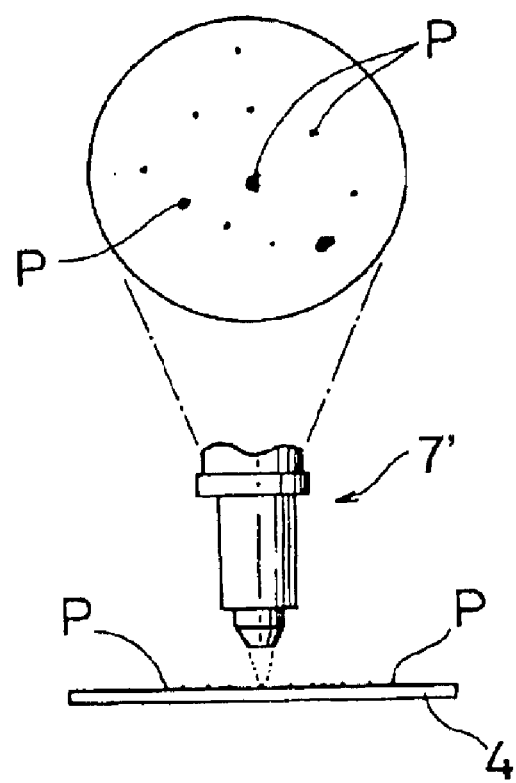

Since the dust-collecting electrode 4 has a smooth surface, the floating dusts P are collected in a state that they are simply placed on the surface individually. Therefore, in the case of the microscopic observation, especially by using the dust-collecting electrode 4 wherein the transparent electrode is applied to the surface of the glass plate, the microscope 7' can be used to observe the floating dusts P on the dust-collecting electrode 4 as they are, as shown in FIG. 5. Thus, it is extremely easy to measure shapes and the number of the floating dusts P.

Next, a method of measuring a quantity of the floating dusts in the atmosphere per unit volume will be explained.

In this case, a device similar to the device shown in FIG. 1 is used to collect the floating dusts P in the atmosphere. Prior to the collection, an electronic balance or the like is used to measure a weight of the dust-collecting electrode 4 in a clean state. Thereafter, the pump 2 is driven with a predetermined flow rate while applying a high voltage to the discharge electrode 3 to collect the floating dusts P on the dust-collecting electrode 4. A total volume of the atmosphere sucked into the collecting container 1 can be obtained from the flow rate of the pump 2 and an operating time. When the total volume reaches a specific quantity, the pump 2 is stopped, and the weight of the dust-collecting electrode 4, in a state where the floating dusts P are collected, is measured by the electronic balance or the like. The weight difference of the dust-collecting electrode 4 before and after the operation represents the weight of the floating dusts P in the atmosphere sucked into the collecting container 1.

Since the dust-collecting electrode 4 is formed of a glass plate and a transparent electrode coated thereon or a metal plate, the dust-collecting electrode 4 does not absorb water. Thus, the quantity of the floating dusts P measured as described above is accurate without errors.

Next, a method of determining a chemical component contained in the floating dusts P in the atmosphere will be explained.

In this case, also, a similar device shown in FIG. 1 is used to collect the floating dusts P. While sucking the atmosphere with the pump 2, a high voltage is applied to the discharge electrode 3 to collect a proper amount of the floating dusts P on the dust-collecting electrode 4. Since the floating dusts P collected on the dust-collecting electrode 4 as described above are in a dispersed state on the smooth flat surface, it is easy to extract the floating dusts P in bulk from the surface of the dust-collecting electrode 4, or easy to extract each particle individually.

Therefore, it is possible to use any one or a combination of the devices for identifying the chemical component, i.e. a liquid chromatograph mass spectrometer, gas chromatograph mass spectrometer, high-frequency induction binding plasma mass spectrometer, spectrophotometer and fluorescence X-ray analyzer. After the floating dusts P collected in the above process are processed according to each device, the floating dusts P are subjected to the analysis to thereby accurately identify the chemical component contained in the floating dusts P.

Figure 6:
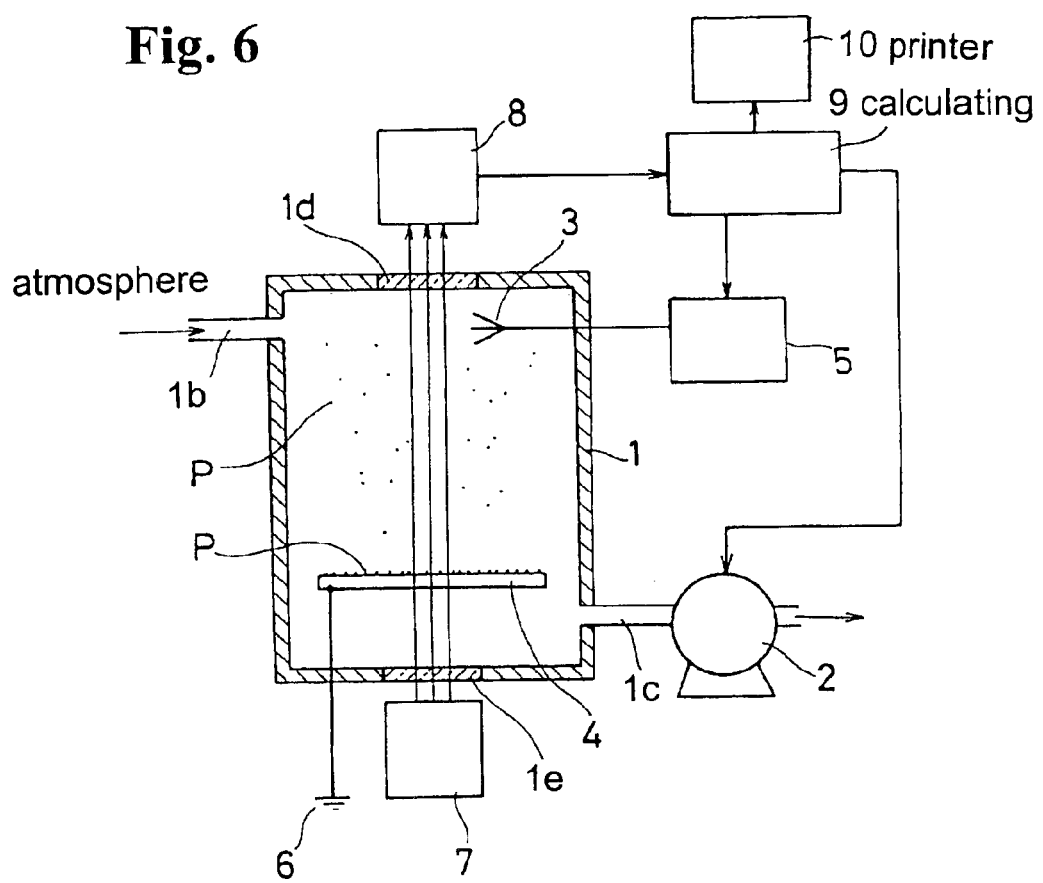

FIG. 6 is a block diagram showing a structure of another embodiment according to the present invention.

A collecting container 1 includes an inlet port 1b and a communicating port 1c connecting to an inlet port of the pump (compressor) 2. The atmosphere is sucked into the collecting container 1 through the inlet port 1a. The collecting container 1 is provided with a discharge electrode 3 at an upper part thereof and a dust-collecting electrode 4 disposed at the bottom thereof. Incidentally, the collecting container 1 includes a lid or a door (not shown) for taking out or putting the dust-collecting electrode 4 therein. In a state where the lid or door is closed, the collecting container 1 communicates with the outside through only the inlet port 1b and the communicating port 1c.

A high voltage from the high voltage source 5 is applied to the discharge electrode 3 to thereby ionize the air around the discharge electrode 3 and generate the single polarity ions.

The dust-collecting electrode 4 is a transparent flat plate-shape electrode having a smooth surface. For example, the dust-collecting electrode 4 is formed of a glass plate or a plastic plate with a transparent electrode coating. The dust-collecting electrode 4 is connected to the ground potential 6.

A transparent window 1e formed of a glass plate is provided at a bottom of the collecting container that corresponds to a position just under a center of the dust-collecting electrode 4. Also, a similar transparent window 1d is provided at a top of the container at a position vertically straight above the window 1e. A light source 7 is disposed under the window 1e for irradiating parallel beams such as laser light or light from a lamp in a vertical upper direction. A light detector 8 is disposed above the window 1d for detecting an intensity of the parallel beams from the light source through the dust-collecting electrode 4.

A detection output from the light detector 8 is sent to an operation control device 9. In the operation control device 9, a relationship between the transmitted light intensity and a quantity of the floating dusts P detected by the light detector 8 is stored in advance. The relationship is obtained through a calibration using an output of the light detector 8 in a state where the floating dusts P are not collected on the dust-collecting electrode 4, and an output of the light detector 8 in a state where a known amount of the floating dusts P is collected on the dust-collecting electrode 4.

The operation control device 9 supplies an operation control signal to the pump 2 and the high voltage source 5. A printer 10 is connected to the operation control device 9, so that real time information regarding a concentration of the floating dusts P on the dust-collecting electrode 4 based on the output of the light detector 8 can be printed out.

The above embodiment can be used as a device for collecting the floating dusts P in the atmosphere as well as a device for measuring a concentration of the floating dusts P in the atmosphere.

When the present embodiment is used as the concentration measuring device, while the high voltage is applied to the discharge electrode 3 and the pump 2 is operating, the information regarding the quantity of the floating dusts P on the dust-collecting electrode 4 based on an output of the light detector 8 is output to the printer 10 at every predetermined time. As the pump 2 is sucking a constant quantity of the atmosphere per unit time, a total volume of the atmosphere sucked in the collecting container 1 from a starting point to any elapsed time can be obtained. Therefore, the information regarding the quantity of the floating dusts P sequentially output to the printer 10 represents the quantity of the floating dusts P contained in the total volume of the atmosphere sucked in the collecting container 1 up to the respective time points. Also, by calculating a difference of the collected quantities at specific time points, a change in the concentration of the floating dusts P in the atmosphere with time can be obtained.

In the case that the present embodiment is used as a device for collecting the floating dusts P, the collecting device is started after a desired particle concentration, i.e. a collected quantity, is set at the operation control device 9. When the concentration based on the output of the light detector 8 reaches the set value, the operation control device 9 automatically stops the pump 2 and the discharge electrode 3. Thus, a predetermined amount of the floating dusts P can be collected on the dust-collecting electrode 4.

It is possible to use the laser diffraction particle size analyzer to measure a particle size distribution of the floating dusts P collected on the transparent plate-shape dust-collecting electrode 4 with a high resolution in a wide range of size distribution. More specifically, the laser diffraction particle size analyzer measures the spatial intensity distribution of the diffracted/scattered light obtained by irradiating the laser beam to the dispersed particles. Then, the spatial intensity distribution is converted to the particle size distribution based on the scattering theory of Mie and the diffraction theory of Fraunhofer. The laser diffraction particle size analyzer can determine the particle size distribution with a high resolution in a wide range of particle diameters as long as a concentration of the particles is high enough to obtain a sufficient intensity of the diffracted/scattered light and not cause multi-scattering.

Also, the floating dusts P collected by the above-explained embodiment are adhered to the transparent flat plate-shape dust-collecting electrode 4. Thus, when the microscope is used, the particle image is not influenced by a background image as in the conventional collecting method using a filter, so that a clear image can be obtained.

Figure 7:
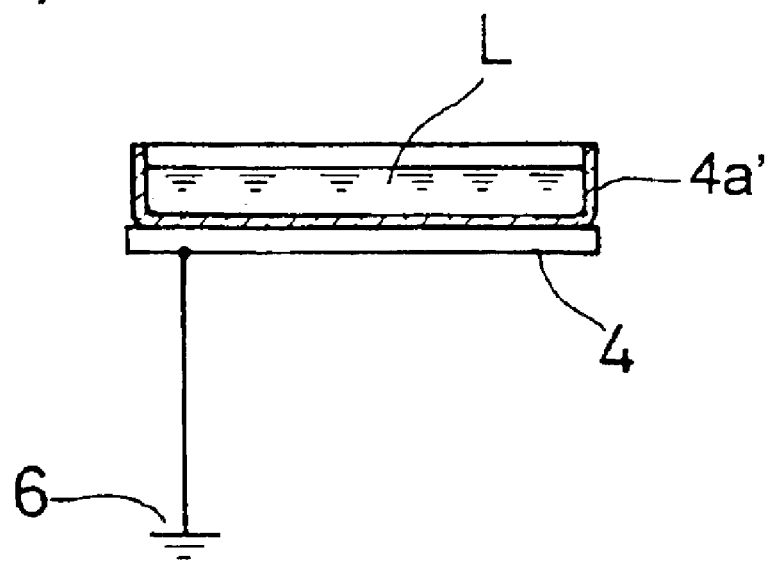

Incidentally, in the above embodiment, the transparent flat plate-shape electrode is used as the dust-collecting electrode 4 to collect the floating dusts P. As shown in FIG. 7, a collecting part 4a' in a Petri dish shape is formed of a transparent material with a transparent electrode coating, and is mounted on an upper surface of the transparent flat plate-shape dust-collecting electrode 4. Then, a liquid L is poured in the collecting part 4a', and the charged floating dusts P are collected in the liquid L. In this case, the calibration is performed in a state where the liquid L is filled in the collecting part, and the output of the light detector 8 represents the information regarding the quantity of the floating dusts P, as in the above case.

Also, in the case that the floating dusts P are collected in the liquid L, when the laser diffraction particle size analyzer measures the particle size distribution, the particles are dispersed in a medium liquid and subjected to irradiation of the laser beams, i.e. wet type measurement. It is preferable to use the same liquid for the liquid L as the medium liquid used in the wet type measuring.

Figure 8:
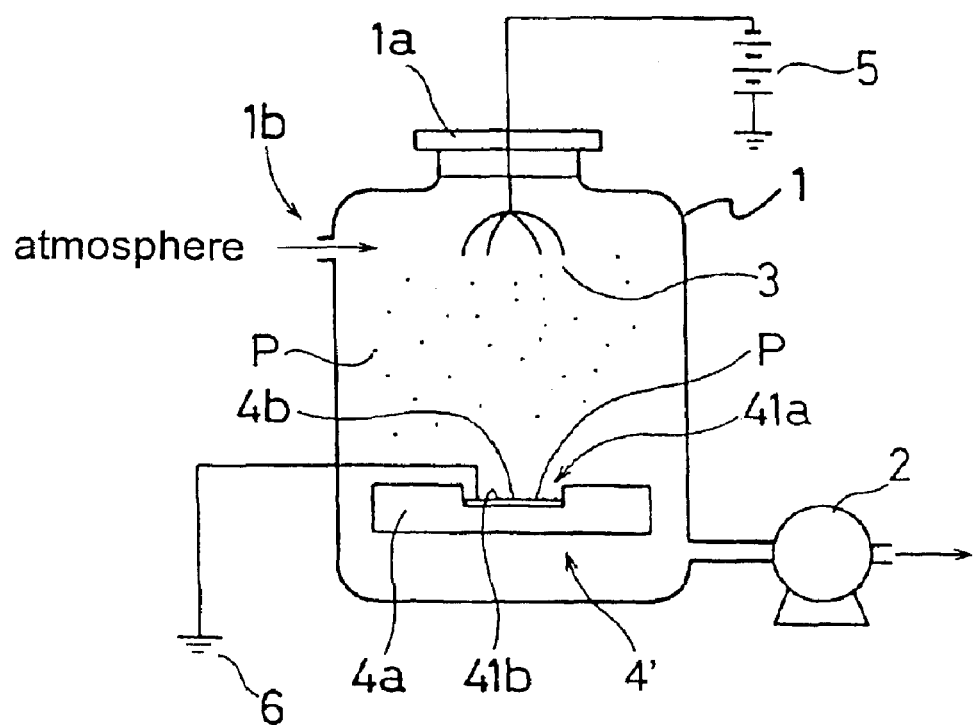
Figure 9:
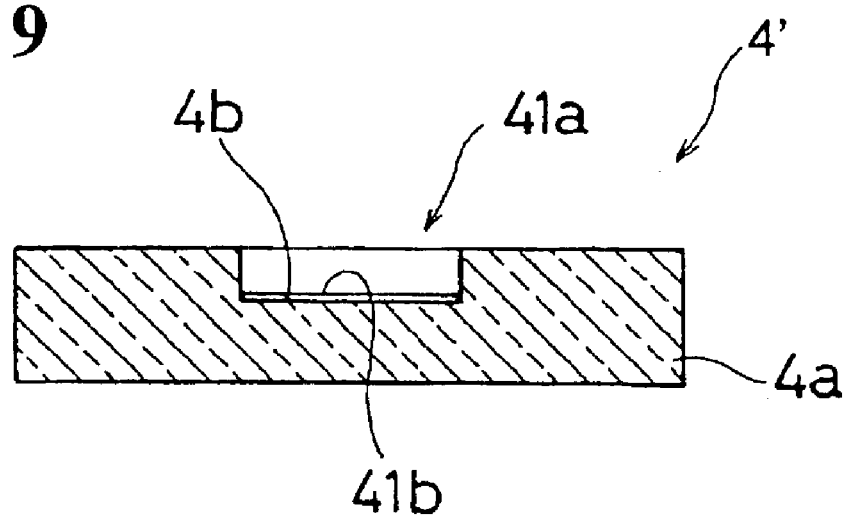

FIG. 8 is a schematic diagram showing a structure of another embodiment according to the invention, and FIG. 9 is a sectional view showing a structure of a dust-collecting electrode 4'.

A collecting container 1 with a lid 1a includes an inlet port 1b of the atmosphere and a communicating port 1c communicating with an inlet of a pump (compressor) 2. While the lid 1a is closed, the atmosphere is sucked in the collecting container 1 through the inlet port 1b by operating the pump 2.

The collecting container 1 is provided therein with a discharge electrode 3 at an upper portion thereof and a dust-collecting electrode 4' facing the discharge electrode 3 at a lower portion thereof. A high voltage is applied to the discharge electrode 3 from a high voltage source 5 to ionize the air near the discharge electrode 3 and generate the single polarity ions.

As shown in FIG. 9, the dust-collecting electrode 4' is structured such that a recessed portion 41a is formed on one side of a transparent glass plate 4a and a transparent electrode film 4b is formed on a bottom surface 41b of the recessed portion 41a. In the collecting container 1, the dust-collecting electrode 4' is positioned such that the surface with the recessed portion 41a faces the discharge electrode 3, i.e. faces upwards. The transparent electrode film 4b is connected to a ground potential 6. As a material for the transparent electrode film 4b, for example, such known conductive materials as ITO and $SnO_2$ can be used. Also, instead of the glass plate 4a, a transparent plastic, for example, a plate formed of an acrylic resin and the like, can be used. Further, a sheet of plate and another sheet of plate with a hole may be bonded together to form the recessed portion of the dust-collecting electrode.

With the structure as described above, when a high voltage is applied to the discharge electrode 3 while operating the pump 2, the surrounding air is ionized to produce the single polarity ions. The single polarity ions are moved toward the dust-collecting electrode 4' by the potential difference between the transparent electrode film 4b and the discharge electrode 3. While moving, the single polarity ions contact and charge the floating dusts P in the atmosphere sucked into the collecting container 1. Due to the potential difference between the discharge electrode 3 and the transparent electrode film 4b (the bottom surface 41b of the recessed portion 41a of the dust-collecting electrode 4'), the charged floating dusts P are collected on the transparent electrode film 4b in a dispersed state at random. At this time, since the transparent electrode film 4b is grounded, even if a large quantity of the floating dusts P is collected, the collecting efficiency is not lowered. Thus, the floating dusts P can be continuously collected with a high efficiency.

Figure 10:
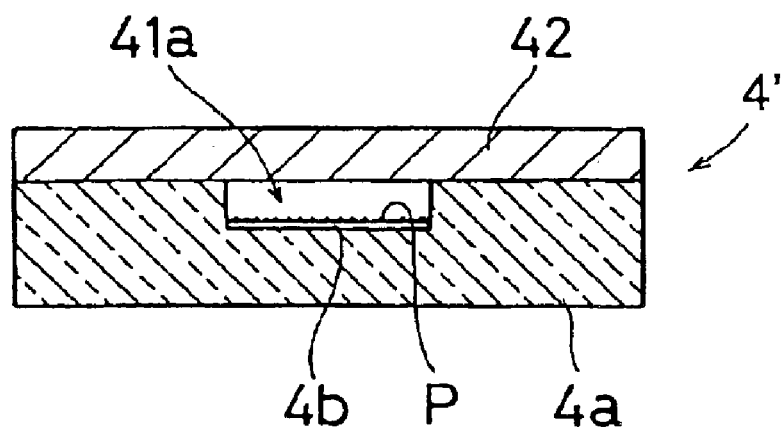

The floating dusts P collected as described above are adhered on the transparent electrode film 4b in the recessed portion 41a of the dust-collecting electrode 4'. Thus, the respective particles can be easily taken out, so that these particles can be easily used for the analyses using various instruments. Also, since the dust-collecting electrode 4' is transparent, a clear particle image can be obtained when a microscope is applied to the observation. Further, as shown by a sectional view in FIG. 10, a lid 42 may cover the recessed portion 41a after the floating dusts P are collected, so that the collected floating dusts P can be held in a collected state without contacting them.

Also, a laser diffraction particle size analyzer can measure a particle size distribution of the floating dusts P over a wide range of the particle diameters at a high resolution, in a manner as shown below.

Figure 11:
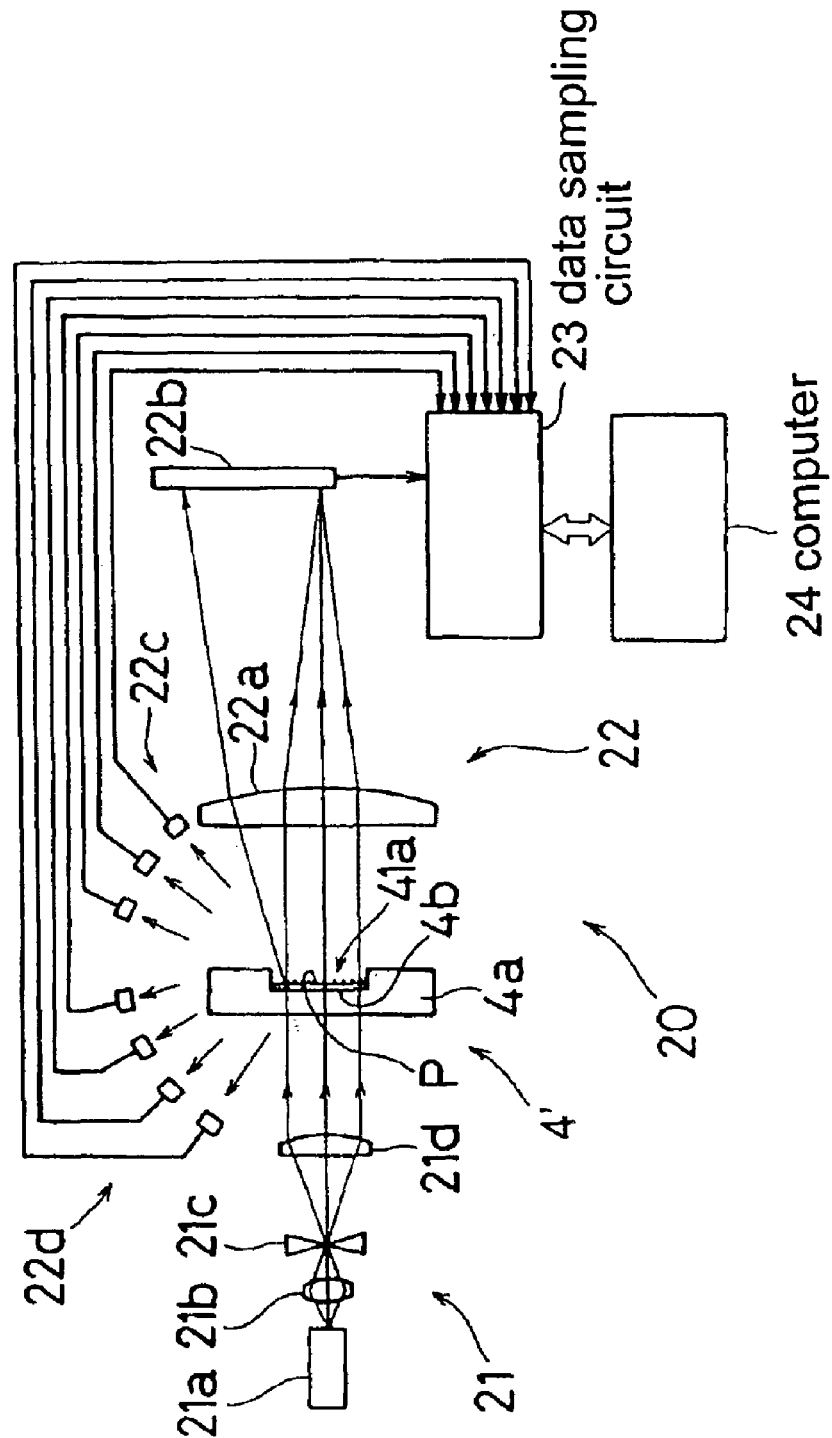

FIG. 11 is a schematic diagram showing a structure of a laser diffraction particle size analyzer, wherein a schematic diagram showing an optical structure and a block diagram showing an electric structure are combined.

A laser diffraction particle size analyzer 20 includes an irradiation optical system 21 for irradiating parallel laser beams to the particles; a measuring optical system 22 for measuring a spatial intensity distribution of the diffracted/scattered light from the particles; a data sampling circuit 23 for sampling data from the measuring optical system 22; and a computer 24 for calculating the particle size distribution of the particles from the spatial intensity distribution data of the diffracted/scattered light sampled by the data sampling circuit 23.

In the device as shown in FIG. 11, the dust-collecting electrode 4' with the floating dusts P collected in the recessed portion 41a is disposed vertically between the irradiation optical system 21 and the measuring optical system 22, so that the laser beams irradiate perpendicular to the electrode.

Since the structure and the measuring method of the apparatus are the same as those of the apparatus as shown in FIG. 4, explanations thereof are omitted.

It is necessary to calibrate the laser diffraction particle size analyzer 20 to obtain an accurate particle size distribution. For the calibration, it is necessary to measure a spatial intensity distribution of the standard particles having known particle diameters in a dispersed state under the same conditions for measuring the actual dusts. In the dust-collecting electrode 4' of the embodiment according to the invention, the recessed portion 41a is formed on the transparent member to collect the floating dusts P on the bottom surface of the recessed portion 41a. Therefore, it is possible to place the standard particles dispersed in a medium liquid, such as water, in the recessed portion 41a so that the laser beams can be irradiated thereto. This enables to calibrate the device with the same collecting electrode 4' as that for measuring the spatial intensity distribution of the diffracted/scattered light from the floating dusts P. Therefore, it is possible to obtain an accurate particle size distribution without variations in the particle size distribution caused by a shape of the dust-collecting electrode 4'.

Incidentally, the transparent electrode film 4b of the dust-collecting electrode 4' may be coated on any area in addition to the bottom surface 41b of the recessed portion 41a. However, it is preferable to coat the transparent electrode film 4b only on the bottom surface 41b to collect the floating dusts P, so that the floating dusts P are collected in the recessed portion 41a in a high density.

Figure 12:
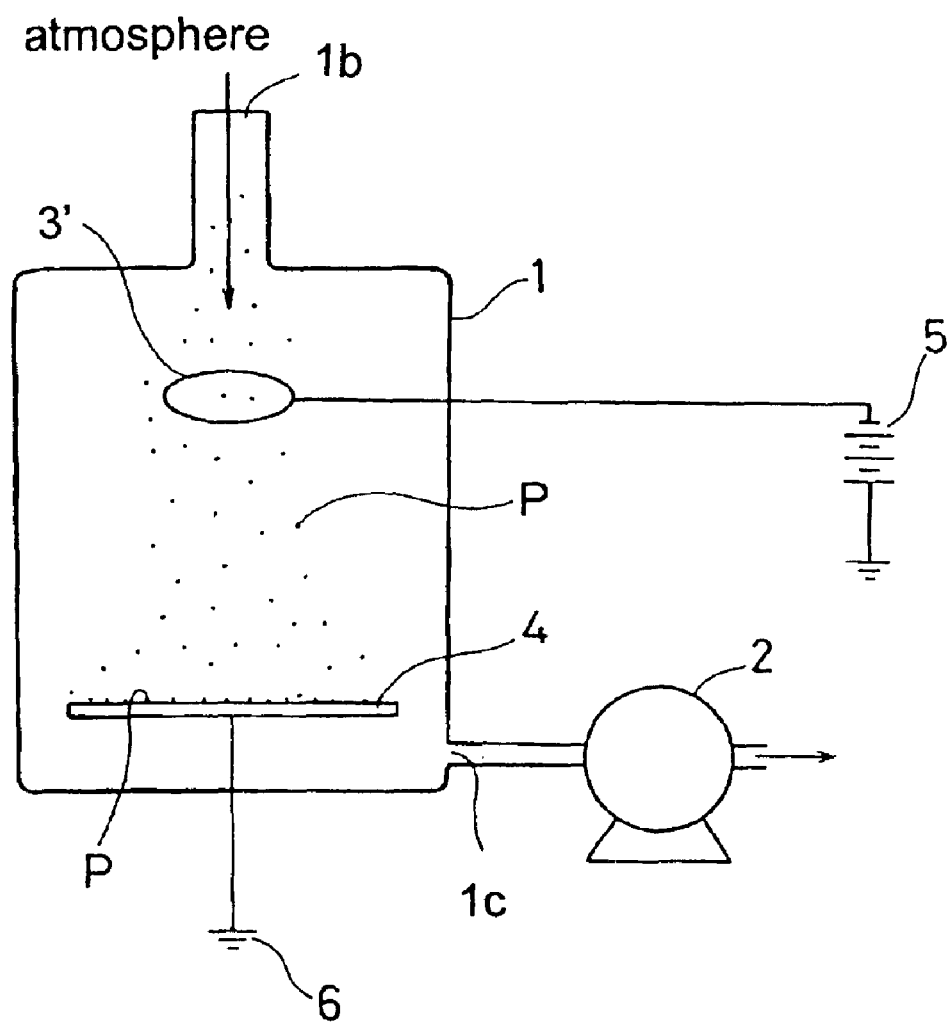

FIG. 12 is a schematic view showing a structure of a collecting device, wherein a discharge electrode according to the invention is applied.

As in the device described previously, the collecting container 1 includes the inlet port 1b and the communicating port 1c communicating with the pump 2. The atmosphere is sucked in the collecting container 1 through the inlet port 1b by operating the pump 2.

In the collecting container 1, a discharge electrode 3' is disposed on the upper portion thereof and the dust-collecting electrode 4 facing the discharge electrode 3 is disposed on the lower portion thereof.

The discharge electrode 3' is formed of a circular ring of a wire made of a metal having a good conductivity, such as a copper alloy. The discharge electrode 3' is disposed such that a surface formed by the circular ring is positioned substantially parallel to the surface of the dust-collecting electrode 4. Although a diameter of the circular ring is not specially limited, the ring may have the same size as the dust-collecting electrode 4, for example, in the order of several cm. A high voltage from the high voltage source 5 is applied to the discharge electrode 3', so that the air near the discharge electrode 3' is ionized to generate the single polarity ions.

The dust-collecting electrode 4 is formed of a metal plate or a transparent plate such as a glass plate or the like. A surface of the duct-collecting electrode may be coated with a transparent electrode film. The dust-collecting electrode 4 is connected to the ground potential 6.

In the same manner as the previous embodiments, when the high voltage is applied to the discharge electrode 3' while operating the pump 2, the discharge electrode 3' ionizes the surrounding air to generate the single polarity ions. At this time, since the discharge electrode 3' is formed in the ring shape, the single polarity ions can be concentrically produced in the vicinity of the ring. The single polarity ions move toward the dust-collecting electrode 4 due to the potential difference between the discharge electrode 3' and the dust-collecting electrode 4. While moving, the single polarity ions contact and charge the floating dusts P in the collecting container 1. The charged floating dusts P are collected on the dust-collecting electrode 4 by the potential difference between the discharge electrode 3' and the dust-collecting electrode 4.

In the above embodiment, the discharge electrode 3' has a simple shape and structure with the ring of the metal wire. The discharge electrode 3' has efficiency same or higher than that of the conventional discharge electrode shown in FIG. 14. Therefore, the discharge electrode 3' can collect the floating dusts P sucked in the collecting container 1 at the same or higher efficiency than that of the conventional discharge electrode. Further, the discharge electrode 3' of the present embodiment is formed of the simple metal wire ring. Thus, it is easy to manufacture, and the cost thereof can be reduced. Moreover, it is easy to reproduce the products in the same shape, thereby reducing variances in the products.

Figure 13:
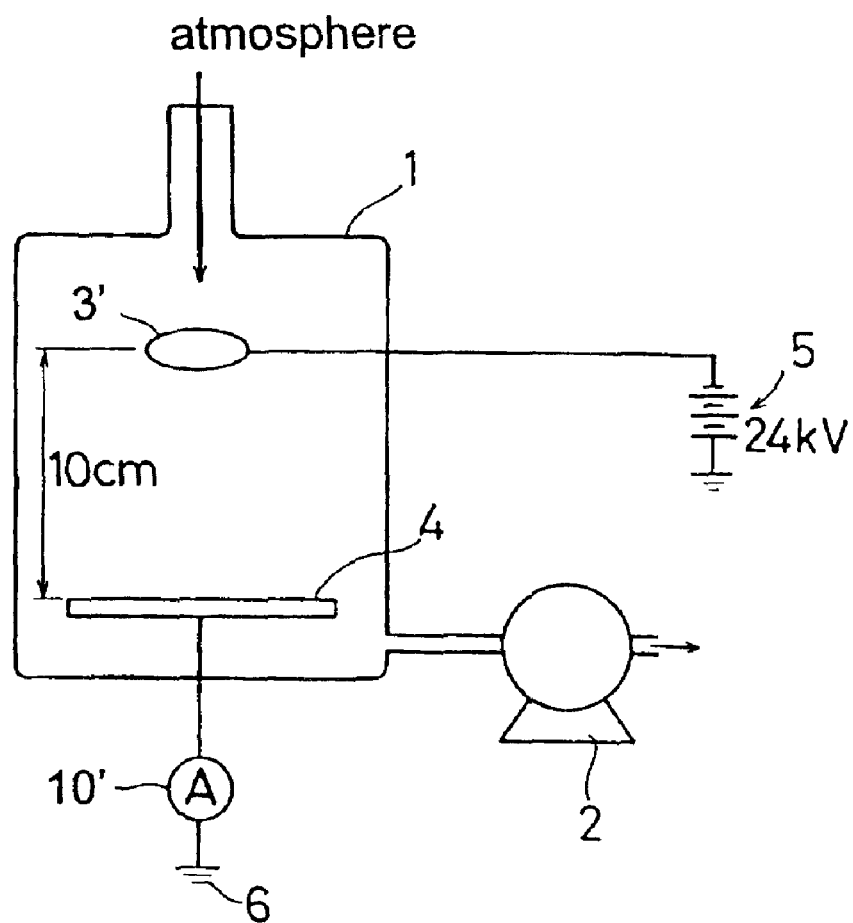

FIG. 13 is a schematic view of an experimental device for measuring the discharge efficiency of the discharge electrode 3' in the ring shape. In this device, the same electrostatic type dust-collecting device as that of the above-described embodiment is used. An ammeter 10' is connected in series between the dust-collecting electrode 4 and the ground potential 6 to thereby measure a current flowing therebetween. The electrostatic collecting device is operated under the same conditions as the normal conditions, using the ring-shape discharge electrode 3' and the conventional discharge electrode (a bundle of three hundred metal wires). The ammeter 10' measures the currents in the cases using the two electrodes for comparison.

As the operational conditions, the potential difference between the discharge electrode 3' and the dust-collecting electrode 4 was 24 kV; a distance between the electrodes was 10 cm; and a volume rate of the atmosphere sucked by the pump 2 was 17 liters/min.

Also, metal wires made of the same material with the same thickness were used for the ring shape discharge electrode 3' and the control discharge electrode as shown in FIG. 14. The results are shown in Table 1.

TABLE 1

| Electrode shape | Ring (embodiment) | Bloom (control) |
| --- | --- | --- |
| Current | 3 $\mu$A | 2 $\mu$A |

The ring-shape discharge electrode 3' of the invention uses less metal wires and has a simple shape and structure. As apparent from the above table, the discharge electrode 3' shows a larger current compared to the conventional discharge electrode using a larger number of metal wires. Thus, it is found that a larger number of the ions are generated according to the present invention under the same operating conditions.

In the above embodiment, the discharge electrode 3' is formed in the ring shape. However, the present invention is not limited thereto and the shape may be a loop of any shape other than the ring. The discharge efficiency of those loops is confirmed to be the same as that of the ring shape. Also, although the size of the loop is not specially limited, it is preferable that the loop size be the same as that of the dust-collecting electrode.

Figure 15:
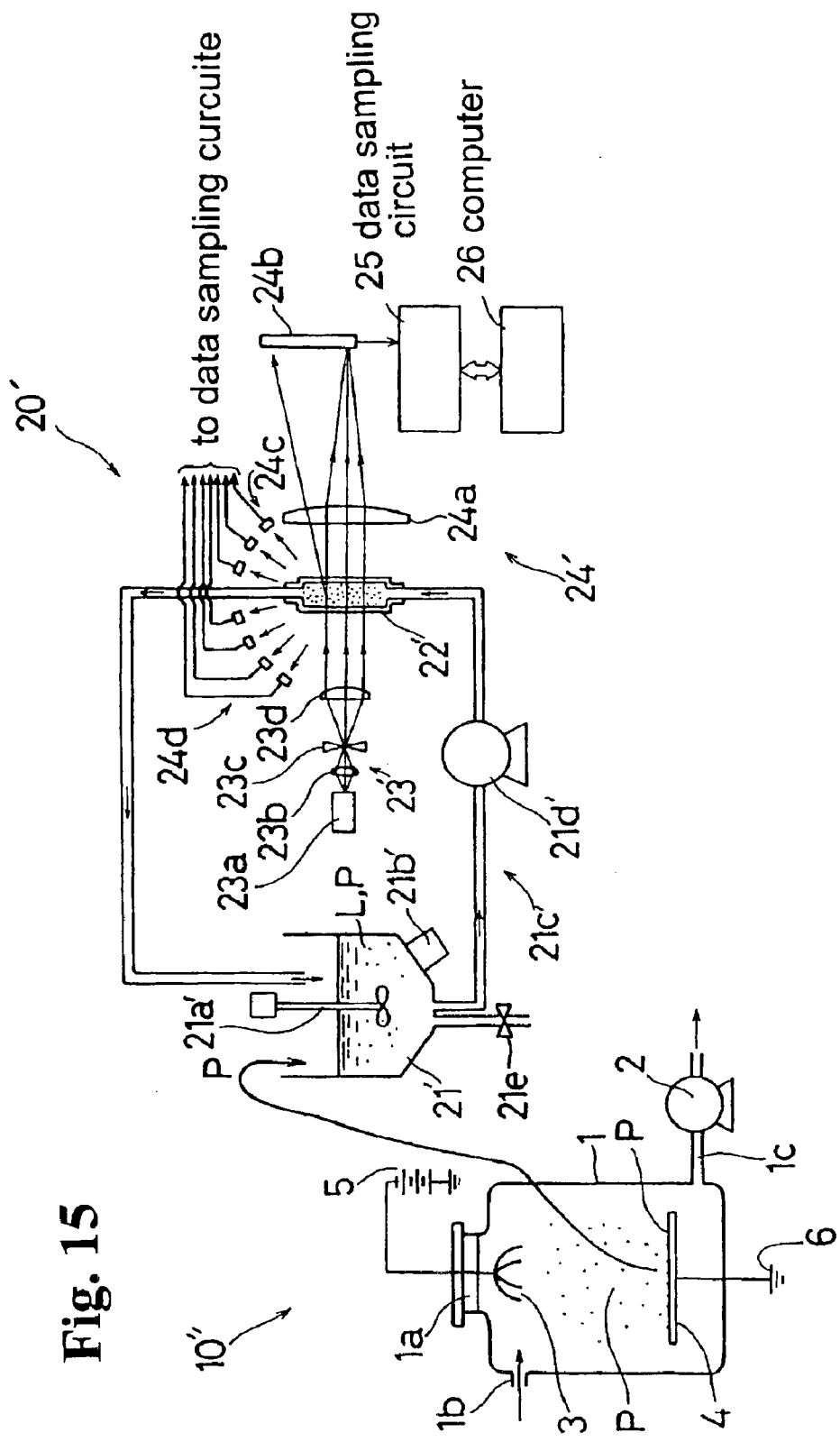

FIG. 15 is a schematic diagram of an embodiment according to the present invention. A collecting device 10" and a laser diffraction particle size analyzer 20' for measuring a particle distribution and a particle concentration of yellow sand particles or pollens collected by the collecting device 10" are shown together.

Similar to the embodiments described previously, the collecting device 10" is formed of the collecting container 1, the pump 2, the discharge electrode 3 and the dust-collecting electrode 4. The collecting container 1 with a lid 1a includes an inlet port 1b and a communicating port 1c communicating with the pump 2. When the pump 2 is operated with the lid 1a closed, the atmosphere is sucked into the collecting container 1 through the inlet port 1b. In the collecting container 1, the discharge electrode 3 is disposed at an upper portion thereof and the dust-collecting electrode 4 facing the discharge electrode 3 disposed at a lower portion thereof. A high voltage is applied to the discharge electrode 3 from the high voltage source 5 to ionize the air near the discharge electrode 3 to generate the single polarity ions.

The dust-collecting electrode 4 is connected to the ground potential 6. The single polarity ions move toward the dust-collecting electrode 4 by the potential difference between the dust-collecting electrode 4 and the discharge electrode 3. The single polarity ions contact and charge the floating dusts P, such as the yellow sand particles or pollens, contained in the atmosphere in the collecting container 1. The charged particles P including the yellow sands or pollens move toward the dust-collecting electrode 4 by the potential difference between the discharge electrode 3 and the dust-collecting electrode 4 to accumulate on the dust-collecting electrode 4.

As the dust-collecting electrode 4, a metal having a smooth surface, or a transparent glass or plastic with a transparent electrode can be used. The particles P of the collected yellow sands or pollens can be easily extracted individually. Therefore, when a microscope is used for the observation, a clear image can be obtained. Also, in the case that various instruments are used to analyze the particles P, it is extremely easy to collect and prepare the particles.

In the case of the particle size distribution measurement, the laser diffraction-scattering type particle size distribution measuring device 20' measures the whole particles P collected on the dust-collecting electrode 4. FIG. 15 shows an example of a system for wet type measurement. In the case of the wet type measurement, a medium liquid L consisting of, for example, a distilled water or an organic solvent, or a liquid with a dispersing agent such as a surfactant, is filled in a dispersing tank 21', and the particles P collected on the dust-collecting electrode 4 are dispersed therein.

The particles P are dispersed into the dispersing tank 21' in such a way that the dust-collecting electrode 4 is taken out of the collecting container 1 by removing the lid 1a and placed in the dispersing tank 21' to thereby transfer the floating particles on the dust-collecting electrode 4 into the medium liquid L. Alternatively, as shown in FIG. 7, the collecting part 4a' in a Petri dish shape made of a conductive material is mounted on the dust-collecting electrode 4. The collecting part 4a' contains the same medium liquid L as the above-mentioned medium liquid L. The floating particles P are collected in the medium liquid L in the collecting part 4a'. The medium liquid L in the collecting part 4a' containing the floating particles P may be guided into the dispersing tank 21' by a pump (not shown), or may be poured into the dispersing tank 21' by hand.

The dispersing tank 21' includes an agitator 21a' and an ultrasonic vibrator 21b'. Also, the dispersing tank 21' is communicated with one end of a circulation pipe 21c' at the bottom portion thereof. The circulation pipe 21c' is communicated with a flow cell 22' through a circulation pump 21d' and further extended to an upper portion of the dispersing tank 21' from an exit of the flow cell 22' to open thereat. Also, the dispersing tank 21' is provided with a discharge valve 21e for discharging the contents of the tank from the bottom portion thereof.

When the agitator 21a' and the ultrasonic vibrator 21b' are operated in a state where the particles P are poured in the medium liquid L in the dispersing tank 21', the particles P are uniformly dispersed and, at the same time, bubbles contained in the medium liquid L are removed. After the medium liquid L and the particles P dispersed therein flow through the flow cell 22' through the circulation pipe 21c' by operating the circulation pump 21d', they are returned to the dispersing tank 21'.

The measuring portion of the laser diffraction particle size analyzer 20' is formed of the flow cell 22', an irradiation optical system 23' for irradiating laser beams to the flow cell 22', and a measuring optical system 24' for measuring a spatial intensity distribution of the diffracted/scattered light from the irradiation optical system 23'.

The irradiation optical system 23' is formed of a laser beam source 23a, a condenser lens 23b, a spatial filter 23c and a collimate lens 23d, so that the laser beams from the laser beam source 23a are irradiated to the flow cell 22' as parallel beams. The laser beams irradiated to the flow cell 22' are diffracted or scattered by the particles P in the medium liquid L flowing therein. The spatial intensity distribution of the diffracted/scattered light is measured by the measuring optical system 24'.

The measuring optical system 24' is formed of a condenser lens 24a; a ring detector 24b disposed on the light axis of the irradiation optical system 23'; front wide-angle scattered light sensors 24c disposed outside of the light axis; and side/backside scattered light sensors 24d disposed on a side and a backside (on the side of the irradiation optical system 23') of the flow cell 22'. The ring detector 24b is an optical sensor array formed of concentrically arranged light sensors with respectively different radiuses and light receiving surfaces in a shape of a ring-shape, ½ ring-shape or ¼ ring shape. An intensity distribution of the diffracted/scattered light focused by the condenser 24a within a predetermined front angle can be detected. Therefore, with the measuring optical system 24' composed of these sensors, it is possible to measure the spatial intensity distribution of the diffracted/scattered light from the particles P dispersed in the medium liquid L in the flow cell 22' over a wide range from the front micro-angle to the backward.

The light intensity detection signal for every diffraction-scattering angle by the measuring optical system 24' is amplified by the data sampling circuit 25 formed of amplifiers and A–D converters, then digitalized and sent to the computer 26 as the spatial intensity distribution data of the diffracted/scattered light.

The computer 26 calculates the particle size distribution of the particles P in the flow cell 22', which cause the diffraction and scattering of the laser beams, from the spatial intensity distribution of the diffracted/scattered light through the operations based on the scattering theory of Mie and the diffraction theory of Fraunhofer, well known theories in the laser diffraction-scattering type particle size distribution measurement.

In order to calculate a particle size distribution of specific particles, a particle diameter range of the specific particles is determined by, for example, a microscope or the like, and the result is input in the computer 26 in advance. The computer 26 selects a size distribution of particles in the size range corresponding to the specific particles among the size distributions of the whole particles P collected on the dust-collecting electrode 4. The selected distribution is normalized to display on a display device (not shown), or print on a printer (not shown), as the particle size distribution of the specific particles in the atmosphere.

With the structure as described above, the total amount of the atmosphere fed into the collecting container 1 can be obtained from a flow rate and the driving time per unit time of the pump 2. By suitably setting the total amount of the air to be fed into the collecting container 1, when the particles P collected on the dust-collecting electrode 4 are dispersed in the medium liquid L in the dispersing tank 21', the particles P in the medium liquid L in the dispersing tank can have a proper concentration to obtain the spatial intensity distribution of the diffracted/scattered light measured by the measuring optical system 23'. Thus, the particle size distribution of the particles P can be measured at a high resolution over the wide range of particle sizes by the laser diffracting-scattering type particle size distribution measuring device 20'.

A predetermined quantity of the atmosphere is sucked into the collecting container 1, and the particles P are collected on the dust-collecting electrode 4. Then, the collected particles P are dispersed in the medium liquid L in the dispersing tank 21' to irradiate the laser beams thereto, and the particle size distribution is obtained from the spatial intensity distribution of the diffracted/scattered light. After the measurement, the discharge valve 21e is opened to discharge the liquid in the dispersing tank 21', and a fresh medium liquid L is poured into the dispersing tank 21'. Then, newly collected particles P on the dust-collecting electrode 4 in the collecting container 1 are dispersed in the medium liquid L to start measuring the spatial intensity distribution. The above process is repeated every predetermined time, and a state of the floating dusts in the atmosphere can be continuously monitored.

The absolute intensity of the diffracted/scattered light is proportional to the concentration of the particles P in the atmosphere. Therefore, when a constant amount of the atmosphere is sucked into the collecting container 1 at every operation, a change in the concentration of the particles P in the atmosphere with time can be monitored from the absolute intensity.

Also, prior to the measurement, the absolute intensity of the scattered light from the standard particles with a known number contained in a unit volume may be determined for the calibration. Accordingly, it is possible to establish a relationship between the diameter and the number of the particles contained in the unit volume from the absolute intensity of the diffracted/scattered light from the particles P and the total amount of the atmosphere sucked into the collecting container 1, i.e. a product of a flow rate of the pump 2 and an operating time. The concentration of the above-mentioned specific particles contained in the unit volume of the atmosphere can be obtained from the relationship and the particle diameter range containing the specific particles.

By repeating the above-mentioned measurement at every specific time, the state of the specific particles in the atmosphere can be continuously monitored. For example, it is possible to give a warning when the concentration of the specific particles exceeds a preset value.

In the above embodiments, the particles P collected on the dust-collecting electrode 4 are dispersed in the medium liquid L. In addition to the wet-type laser diffraction-scattering measurement as mentioned above, the present invention may be applied to the dry-type laser diffraction-scattering measurement without using the medium liquid.

In the case of the dry-type measurement, as shown in FIG. 2, the dust-collecting electrode 4 formed of the transparent plate 4a made of a glass or plastic with the transparent electrode film 4b coated on the surface thereof. Thus, the laser beams are directly irradiated to the dust-collecting electrode 4 on which the particles P are collected, and the spatial intensity distribution of the diffracted/scattered light can be measured, thereby facilitating the measurement process.

Figure 16:
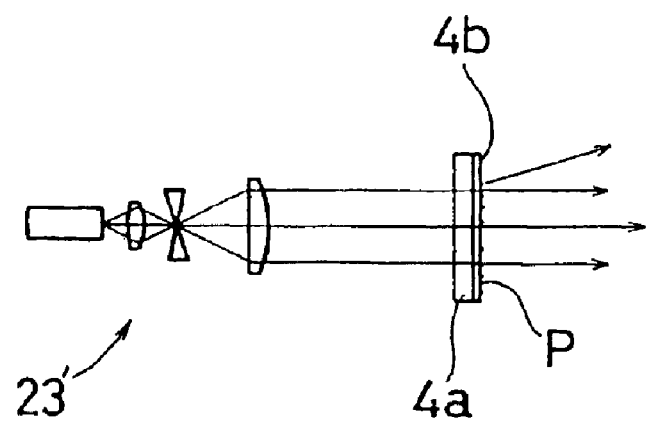

An essential part of the laser diffraction particle size analyzer for the dry-type measurement is shown in FIG. 16. Instead of the flow-cell 22' as shown in FIG. 15, the dust-collecting electrode 4 formed of the transparent plate 4a and the transparent electrode film 4b is disposed for collecting the particles P on the surface thereof. Since the medium liquid is not used, the dispersing tank 21' is not required. Incidentally, other structures are exactly the same as those of the embodiment shown in FIG. 15. As long as the particles P on the dust-collecting electrode 4 have a proper concentration (a quantity of the particles P per unit area), it is possible to accurately measure the spatial intensity distribution of the diffracted/scattered light from the particles P as in the above-described wet-type measurement. Thus, the same benefits as in the wet-type measurement can be obtained.

Also, the microscope can be used to observe the particles by using the dust-collecting electrode 4 formed of the transparent plate 4a and the transparent electrode 4b.

Figure 17:
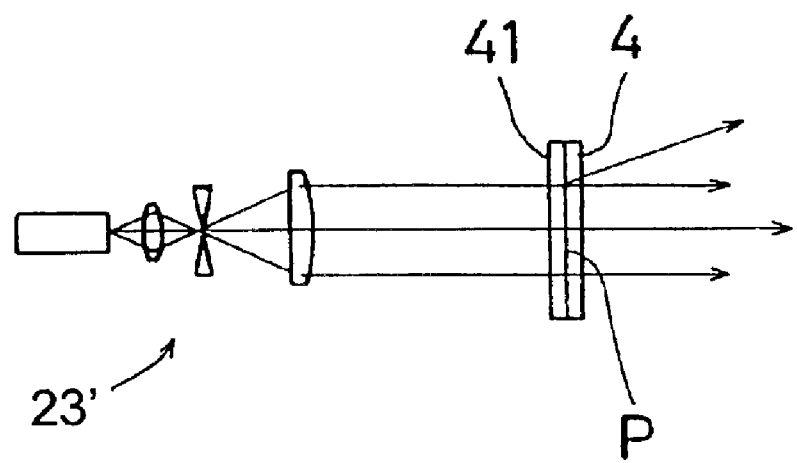

As shown in FIG. 17, in order to prevent the particles P from falling off the dust-collecting electrode 4, the particles P may be sandwiched between a transparent plate 41, such as a glass plate, and the electrode 4, if necessary.

In the embodiments described above, the particles P are collected in the dust-collecting device 1 to determine the particle size distribution. Also, it is possible to measure the shape, kind, number and the like of each particle P through the microscopic observation. In this case, the transparent member can be used as the dust-collecting electrode 4 as mentioned above, so that the electrode 4 can be subjected to the microscopic observation as it is. Almost all particles P contained in the atmosphere sucked in the collecting device 1 are collected on the dust-collecting electrode 4 in the collecting device 1. Thus, the microscope can accurately reveals the whole information of the particles P floating in the atmosphere.

According to the collecting device of the floating dusts in the atmosphere of the invention as described above, the floating dusts in the atmosphere are charged and collected on the dust-collecting electrode formed of the transparent flat plate with the conductive transparent coating. Thus, when the microscope is used, the clear particle image can be obtained without any influence from the background image. Also, since a single floating particle can be easily extracted, the chemical analyses using various instruments, which is impossible in the conventional device using a filter, can be carried out. Further, the conductive transparent coating of the dust-collecting electrode is connected to the ground potential. Thus, the floating dusts can be collected at a high efficiency even when a relatively large quantity of the charged floating dusts is collected, because the potential of the dust-collecting electrode does not change.

Also, by collecting the floating dust in the atmosphere with the collecting device as described above, the laser beam can be directly irradiated to the floating dusts on the dust-collecting electrode by using the laser diffraction particle size analyzer. Also, it is possible to measure the particle size distribution with a high resolution for particles in the order of sub-micron to 10 μm by the laser diffraction-scattering method.

As described hereinabove, the floating dusts in the atmosphere are charged by the single polarity ions generated from the discharge electrode. The charged particles are collected on the dust-collecting electrode formed of the solid member having the continuous surface due to the potential difference between the dust collecting electrode and the discharge electrode. The microscope is used to observe the collected floating dusts, and the clear image can be obtained without the influence of the background when compared with the conventional device where the particles are collected through a filter. Especially, when the glass plate with the transparent electrode coated on the surface thereof is used as the dust-collecting electrode, the microscope can be used to observe the floating dusts collected on the electrode as they are, thereby facilitating the process.

Also, in the present invention, the charged floating dusts are collected on the dust-collecting electrode having the continuous surface. The quantity of the floating dusts in the atmosphere can be measured from the difference in the weights of the dust-collecting electrode before and after the floating dusts are collected thereon. Therefore, it is possible to accurately measure the quantity of the floating dusts with a simple work since the electrode does not absorb water, when compared with the conventional method wherein the floating dusts are collected through the filter and the quantity of the floating dusts in the atmosphere is measured from the weight difference before and after the floating dusts are collected.

Further, the charged floating dusts are collected on the dust-collecting electrode having the continuous flat surface. Thus, the collected floating dusts can be extremely easily extracted individually. It is possible to identify the chemical components contained in the collected floating dusts by using one or a combination selected from a liquid chromatograph mass spectrometer, gas chromatograph mass spectrometer, high-frequency induction binding plasma mass spectrometer, spectrophotometer and fluorescence X-ray analyzer, thereby greatly improving the analyzing accuracy.

Further, according to the measuring device of the present invention, the floating dusts contained in the atmosphere sucked in the collecting container are charged, and the charged particles are collected on the dust-collecting electrode formed of the transparent member. Then, the laser light is irradiated to the dusts to obtain the concentration information of the floating dusts collected on the dust-collecting electrode based on the intensity of the light transmitted-through the dust-collecting electrode. Therefore, it is possible to measure substantially the real time change of the concentration of the floating dusts in the atmosphere.

Also, according to the collecting device of the present invention, the pump can automatically stop sucking the atmosphere at a time when the quantity, i.e. the concentration, of the floating dusts collected on the dust-collecting electrode reaches a preset concentration. Thus, even if the concentration of the floating dusts is changed during the collecting, it is possible to collect the floating dusts with a constant concentration at all times. Thus, a sample in a predetermined optimum concentration can be stably obtained.

As described hereinabove, according to the present invention, the charged floating dusts in the atmosphere are collected on the dust-collecting electrode, which may have the recessed portion formed on the surface of the transparent member and having the transparent electrode film coated on the bottom surface of the recessed portion. Therefore, the microscopic can be used to observe the collected floating dusts as they are to obtain the clear particle image. In addition, the respective particles are easily taken out from the collected dusts and subjected to further analysis. Further, as the lid can cover the recessed portion of the duct-collecting electrode, the collected floating dusts can be preserved without contacting them.

Also, the laser diffraction particle size analyzer irradiates the laser beams directly to the dust-collecting electrode with the collected dusts to measure the diffracted/scattered light so that the particle size distribution can be obtained. Thus, according to the present invention, it is possible to measure the particle size distribution with an extremely simple work at a high resolution in a wide particle range when compared with the conventional method. Prior to the measurement, the medium liquid with the standard particles dispersed therein may be sealed in the recessed portion of the dust-collecting electrode to calibrate the device. Thus, it is possible to eliminate the variances due to the shape of the dust-collecting electrode.

As described hereinabove, according to the present invention, the discharge electrode has the ring shape and the structure is simpler than that of the conventional device. The ring-shape discharge electrode shows the particle collecting efficiency same or higher than the conventional discharge electrode. Since the discharge electrode has the simple shape and structure, the production cost thereof can be reduced as well as the reproducibility is improved, thereby eliminating variances in the products.

As described hereinabove, according to the collecting method of the yellow sands of the invention, the particles floating in the atmosphere can be effectively collected and, at the same time, the respective particles can be easily extracted individually. Thus, the microscope or other various analyzing equipments can be easily used to analyze the yellow sands.

Also, according to the measuring method of the yellow sands of the invention, the particle size distribution of the floating dusts can be measured at a high resolution and, at the same time, the concentration of the particles contained in the atmosphere can be accurately measured. Thus, it is possible to monitor the change in the concentration of the particles and to give a warning according to the results thereof.

As described above, according to the collecting device of the pollens in the atmosphere, the atmosphere is sucked into the collecting container in which the discharge electrode and the dust-collecting electrode are disposed. The floating pollens contained in the atmosphere are charged and collected on the dust-collecting electrode. Thus, the pollens floating in the atmosphere can be sampled quickly without influence of the wind or the like when compared with the conventional collecting method wherein the naturally falling pollens are collected on a glass plate.

Also, the measuring apparatus of the pollens floating in the atmosphere of the invention may be formed of a combination of the collecting device and the laser diffraction particle size analyzer. Accordingly, the particle size distribution of the pollens floating in the atmosphere can be quickly and accurately measured.

Further, according to the measuring method of the pollens floating in the atmosphere, the microscope is used to observe the pollens collected by the above-mentioned collecting device to quickly and correctly determine the shape, kind, number and the like of the pollens floating in the atmosphere. Thus, the real change of the kind and number of the pollens floating in the atmosphere can also be obtained.

The disclosures of Japanese Patent Applications No. 2002-011261 filed on Jan. 21, 2002, No. 2002-142817 filed on May 17, 2002, No. 2002-132613 filed on May 8, 2002, No. 2002-012322 filed on Jan. 22, 2002, No. 2002, No. 2002-194256 filed on Jul. 3, 2002, No. 2002-142012 filed on May 16, 2002, and No. 2002-209713 filed on Jul. 18, 2002 are incorporated in the application.

While the invention has been explained with reference to the specific embodiments of the invention, the explanation is illustrative and the invention is limited only by the appended claims.

What is claimed is:

1. A collecting device for collecting particles floating in an atmosphere, comprising:

a container, a pump for sucking the atmosphere with the particles into the container, a discharge electrode disposed in the container for generating single ions to charge the particles floating in the atmosphere in the container, and a dust-collecting electrode disposed in the container and being formed of a transparent plate having a transparent conductive film on a surface thereof facing the discharge electrode, said dust-collecting electrode being electrically connected to a ground potential for collecting the particles charged in the container when a potential difference is provided to the discharge electrode.

2. A measuring device comprising: the collecting device according to claim 1, a light irradiating device disposed at one side of the collecting device for irradiating light to the dust-collecting electrode, and a detecting device disposed at the other side of the collecting device for detecting an intensity of the light passing through the dust-collecting electrode so that a result of the intensity is outputted as a concentration of the particles.

3. A collecting device according to claim 1, wherein said discharge electrode is formed of a metal wire having a loop shape.

4. A collecting device for collecting pollens floating in an atmosphere comprising the collecting device according to claim 1, said dust-collecting electrode drawing and collecting the pollens when the discharge electrode is provided with potential difference.

5. A collecting device according to claim 4, further comprising means for dispersing the pollens on the dust-collecting electrode, means for irradiating a laser beam to the collected pollens in a dispersed condition, a measuring optical device for measuring a spatial intensity distribution of diffracted and scattered light of the laser by the pollens, and calculating means for measuring a size distribution of the pollens collected on the dust-collecting electrode.

6. A collecting device according to claim 1, wherein said container includes an inlet at an upper portion thereof for introducing the atmosphere in the container, and an outlet at a lower portion thereof for discharging the atmosphere so that the atmosphere sucked by the pump flows from the inlet to the outlet, said discharge electrode and the dust-collecting electrode being disposed adjacent to the inlet and the outlet, respectively, to be vertically spaced from each other.

* * * * *